United States Patent
Agostinelli et al.

(10) Patent No.: US 11,660,160 B2
(45) Date of Patent: May 30, 2023

(54) SYSTEMS AND METHODS FOR DETECTING MAGNETIC MARKERS FOR SURGICAL GUIDANCE

(71) Applicant: ENDOMAGNETICS LTD, Cambridge (GB)

(72) Inventors: Tiziano Agostinelli, Cambridge (GB); Kevin Lorimer, Cambridge (GB); Quentin John Harmer, Cambridge (GB)

(73) Assignee: ENDOMAGNETICS LTD.

( * ) Notice: Subject to any disclaimer, the term of this patent is extended or adjusted under 35 U.S.C. 154(b) by 874 days.

(21) Appl. No.: 16/256,404

(22) Filed: Jan. 24, 2019

(65) Prior Publication Data

US 2019/0223975 A1 Jul. 25, 2019

(51) Int. Cl.
*A61B 5/00* (2006.01)
*A61B 90/00* (2016.01)
*A61B 5/06* (2006.01)
*A61B 34/20* (2016.01)
(Continued)

(52) U.S. Cl.
CPC ............. *A61B 90/39* (2016.02); *A61B 5/062* (2013.01); *A61B 5/064* (2013.01); *A61B 34/20* (2016.02); *G01D 5/20* (2013.01); *A61B 2017/00867* (2013.01); *A61B 2017/00876* (2013.01); *A61B 2034/2051* (2016.02); *A61B 2090/397* (2016.02); *A61B 2090/3908* (2016.02); *A61B 2090/3925* (2016.02); *A61B 2090/3954* (2016.02); *A61B 2090/3958* (2016.02); *A61B 2090/3966* (2016.02);
(Continued)

(58) Field of Classification Search
CPC ...................................................... A61B 90/39
See application file for complete search history.

(56) References Cited

U.S. PATENT DOCUMENTS 4,222,517 A * 9/1980 Richardson ............ G06K 1/125
156/269
5,801,630 A 9/1998 Ho et al.
(Continued)

FOREIGN PATENT DOCUMENTS

| EP | 1933286 | 6/2008 |
|---|---|---|
| JP | 2809870 | 10/1998 |
| WO | 2008/020148 | 2/2008 |

OTHER PUBLICATIONS

Susuma et al. "Dependence of large barkhousen jump on length of a vicoalloy fine wire with torsion stress" IEE Transactions on magnetics vol. 34, Jul. 1998. (Year: 1998).*
(Continued)

*Primary Examiner* — Joseph M Santos Rodriguez
(74) *Attorney, Agent, or Firm* — K&L Gates LLP

(57) ABSTRACT

A detection system and method uses an implantable magnetic marker comprising at least one piece of a large Barkhausen jump material (LBJ). The marker is deployed to mark a tissue site in the body for subsequent surgery, and the magnetic detection system includes a handheld probe to excite the marker below the switching field for bistable switching of the marker causing a harmonic response to be generated in a sub-bistable mode that allows the marker to be detected and localised. The marker implanted may also be shorter than the critical length required to initiate bistable switching of the LBJ material.

20 Claims, 16 Drawing Sheets

(51) Int. Cl.
  *G01D 5/20* (2006.01)
  *A61B 17/00* (2006.01)
(52) U.S. Cl.
  CPC ... *A61B 2090/3987* (2016.02); *A61B 2505/05* (2013.01); *A61B 2562/0223* (2013.01)

(56) References Cited

U.S. PATENT DOCUMENTS

| | | | |
|---|---|---|---|
| 6,230,038 B1* | 5/2001 | von Gutfeld | A61N 5/1049 |
| | | | 128/899 |
| 6,337,627 B1 | 1/2002 | Von Gutfeld et al. | |
| 6,747,559 B2 | 6/2004 | Antonenco et al. | |
| 2003/0085809 A1 | 5/2003 | Antonenco et al. | |
| 2011/0313288 A1* | 12/2011 | Chi Sing | A61B 5/06 |
| | | | 600/437 |
| 2016/0354178 A1 | 12/2016 | Mayes et al. | |

OTHER PUBLICATIONS

Sulla et al., "Utilizing Magnetic Microwires for Sensing in Biological Applications", Journal of Electrical Engineering, vol. 66 No. 7/s, 2015, pp. 161-163.
Extended European Search Report for European application No. 21177738.8, dated Nov. 11, 2021 (9 pages).

* cited by examiner

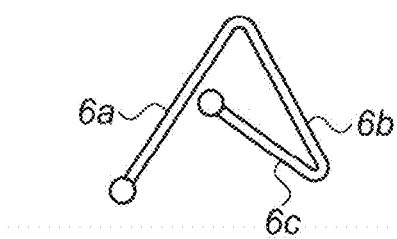
FIG. 9A
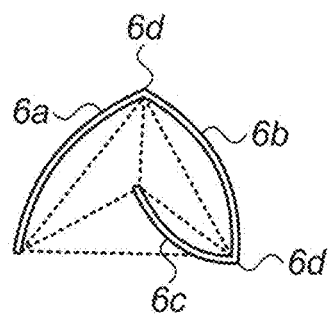
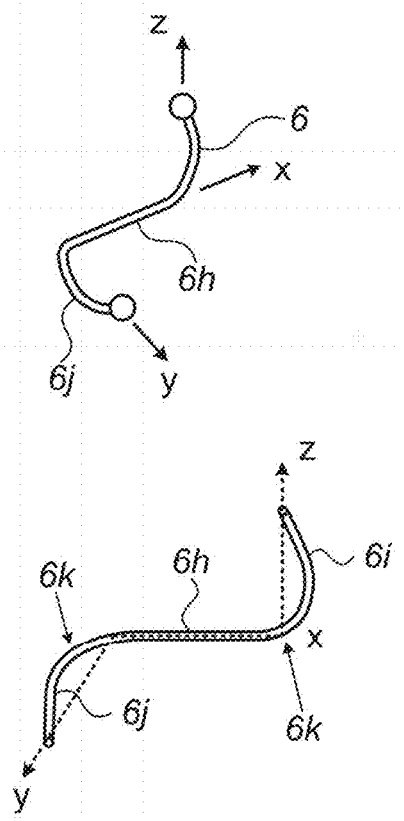
FIG. 9B
FIG. 9D
FIG. 9C
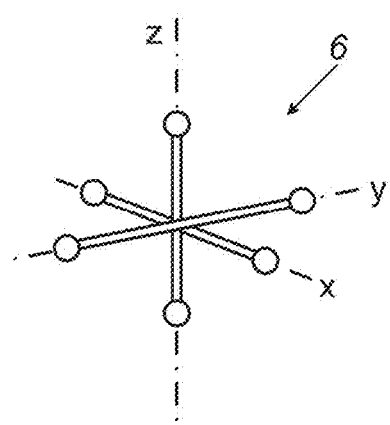

SYSTEMS AND METHODS FOR DETECTING MAGNETIC MARKERS FOR SURGICAL GUIDANCE

CROSS REFERENCE TO RELATED APPLICATIONS

This application claims priority to and benefit from United Kingdom Patent Application No. 1801224.5 filed on Jan. 25, 2018, the entirety of which application is incorporated by reference herein.

FIELD OF THE INVENTION

This invention relates in general to the field of surgical guidance, more specifically to systems and methods for detecting markers that aid in locating a site in the body, for example, a lesion for surgical excision.

BACKGROUND OF THE INVENTION

Markers are used to guide surgeons to a region of interest during a surgical procedure, where the site of interest is not physically visible or palpable, for example a small tumour that needs to be excised. Ideally, such a marker will be deployable through a narrow gauge needle e.g. 18 g to 14 g in order to reduce trauma to the patient. Typically, such markers are less than 5 mm in length so as to be unobtrusive and to minimise trauma. The marker may be placed during a biopsy or other surgical procedure at a site of interest in the body, for example a cancer lesion. The marker is placed under imaging guidance such as ultrasound or X-ray/mammography. During subsequent surgery, the marker is detected and localised using a handheld probe which provides audible, visual or other feedback to the surgeon to guide the surgery. Typically the marker is excised along with the surrounding tissue.

One such approach is to use a marker containing a radioisotope such as Iodine 90 which can be detected using a handheld gamma detection probe. However, use of radioactive materials is closely regulated, making it challenging to set up a radioactive seed programme in all but the largest academic hospital centers.

US 2017/252124 (Cianna Medical) discloses a localization system which uses a combination of radio frequency (RF) and infra red (IR) radiation to detect a marker in the form of an implantable radar antenna. However, this system is limited by the low tissue penetration depth of IR radiation, the need for intimate tissue contact for good IR propagation, and the lack of robustness often associated with an implantable device containing antennae and electronic circuits.

US 2015/264891 (Health Beacons) discloses a further system based on radio frequency identification (RFID) tags that have been used as identity markers for pets and livestock. The drawback with this approach is that the small RFID tag constitutes a dipole antenna which has 'deadspots' when approached perpendicular to the dipole axis. This could cause confusion for surgeons using the system to localize a lesion. Miniaturizing the RFID tag sufficiently for convenient clinical implantation is also challenging.

A further approach is discussed in the Applicant's earlier published patent applications (for example, WO 2011/067576, WO 2014/032235 and WO 2014/140567) and uses magnetic fields and a magnetic marker with high magnetic susceptibility. A handheld probe generates an alternating field which excites a magnetically responsive marker, and detects the responding magnetic field. This approach is effective for deeper sensing and avoids the drawbacks of RF approaches. However, these systems will detect any magnetically responsive material in the vicinity of the probe, such as a ferromagnetic surgical tool or other metallic implanted device. This means that for effective operation they need to be used with non-ferromagnetic surgical instruments and away from other metallic implantables. Additionally, such a probe may respond to iron oxide nanoparticle suspensions used for sentinel node detection in breast cancer.

It has therefore proved problematic to provide a marker and detection system that possesses all the properties required for localising lesions, namely: a marker of a small size (<10 mm long); ability to deliver the marker through a small needle (eg. 16 g-18 g); ability to detect the marker using a handheld probe; and robust for implantation and surgical removal, together with a detection system that is able to distinguish the lesion marker from other magnetically responsive materials.

In the remote field of electronic article surveillance (EAS), technologies are known to improve the signal to noise ratio (SNR) of magnetic detection and to improve the specificity of detection in the presence of other materials. U.S. Pat. No. 4,510,489 for example describes a tag with a strip of magnetostrictive ferromagnetic material that generates a response at a resonant frequency. Other tags employ magneto-acoustic resonance or other non-linear properties of magnetic materials. However, these markers typically need a minimum length of at least 30 to 40 mm to generate a measurable response at low to medium interrogation fields, well above the length acceptable for an implantable marker.

U.S. Pat. No. 4,660,025 to Humphrey discloses the use of an amorphous wire with a large Barkhausen discontinuity in its magnetisation curve as part of an electronic article surveillance system. These 'Large Barkhausen Jump' (LBJ) materials, undergo a rapid reversal of their magnetic polarization when excited by an external magnetic field whose field strength opposing the instantaneous magnetic polarization of the wire exceeds a predetermined threshold value. Thus, the material exhibits bistable behaviour, reversing between two magnetic polarisation states. Each reversal of magnetisation generates a magnetic pulse with harmonic components. The profile and number of harmonics is measured (out to many tens of harmonics) to identify the marker from other materials. The optimum length of the markers is described as between 2.5 and 10 cm in length, again substantially outside the length required for an implantable marker. This approach has the benefit of comprising a single piece of material that generates a strong magnetic response.

Sulla (Utilizing Magnetic Microwires For Sensing In Biological Applications, Jnl. of Elec. Eng., VOL 66. NO 7/s, 2015, 161-163) describes glass coated amorphous microwires for medical applications, in particular as an implant that can be detected magnetically by applying an external field, again using a large Barkhausen jump type bistable behaviour. They conclude that a piece of wire 40 mm in length is required for functional sensing.

However, for this bistable behaviour to be seen two criteria need to be fulfilled: The length of the wire must exceed a 'critical length' value, which for many microwires, is typically >25 mm; and the field must exceed a threshold 'switching field', $H_{SW}$. In addition, the bistable behaviour works best at frequencies less than 3 kHz.

U.S. Pat. No. 6,230,038 to Von Gutfeld describes the use of a magnetic wire with a non-linear response to mark a tumour to guide radiotherapy treatment. The marker comprises either a ferrous material that is driven into the non-linear region of its magnetisation curve, or a bistable LBJ wire driven so that it exhibits bistable behaviour. This approach requires a large external apparatus around the patient with large coils to generate a sufficiently high field to drive the marker into non-linear behaviour. Such apparatus would obscure the surgical site during cancer surgery.

These conditions make this large Barkhausen jump behaviour described in the prior art unsuitable for use as a lesion localisation marker for the following reasons:

The critical length required for the large Barkhausen jump of most such materials is greater than 5-10 mm making them too large for conveniently marking small lesions which may be only a few millimetres in size.

The switching field must be above a threshold in order to drive the bistable behaviour. In article surveillance applications, large area excitation and sensing coils can be employed with diameters in the tens of centimetre range that generate large magnetic fields enabling the presence of a small wire to be detected from a range of one metre or more. However, for surgical guidance, a much more precise localisation of the marker is needed via a handheld or robotically guided detection probe. This limits the size of the detection coils to typically less than 20 mm diameter and thus limits the distance at which a marker can be detected. The detection sensitivity further reduces according to the second order (in the near field) or third order (in the far field) of distance from the coils. If the drive field is also generated in the probe, the detection ability decreases per the fourth or sixth order with distance from the probe. Thus while U.S. Pat. No. 4,660,025 discloses EAS markers excitable with switching fields of 0.6-4.5 Oe (0.06-0.45 mT), and U.S. Pat. No. 6,230,038 with a switching field of at least 1 Oe, the fields that can be generated at around 40 mm from a handheld probe are in the region of $0.5 \times 10^{-3}$-0.05 Oe (0.05-5 µT) when current, voltage, power and temperature range limitations are taken into account i.e. one to two orders of magnitude lower.

For some LBJ materials, the field at which the LBJ response is initiated increases with frequency, meaning that the wires become harder to excite at higher frequencies. For this reason, the prior art specifies frequencies below 3 kHz and preferably well below 1 kHz. This is undesirable for surgical guidance where in order to maximise signal to noise ratio from the very small fields being detected, it is desirable to average the signal over a number of cycles. Higher frequencies allow more averaging without the averaged feedback response to the user appearing to have a lag or delay.

A further drawback of the EAS systems is the large anisotropy of the response from the marker wires, meaning that the response in the axial direction is much greater than the response in the transverse direction. In the EAS application, this does not present a problem because the system only needs to sense the presence of the marker, not its distance from the detector, and so large coils and high field strengths enable satisfactory EAS detection. However, in surgical guidance with a handheld probe, a response that varies depending upon the direction of approach will be confusing to the user because the marker will appear to be a varying distance from the probe depending upon the orientation of approach.

Thus, there remains a need to provide an implantable marker that meets all the requirements of a marker for localising lesions, including small size (<10 mm long); ability to be delivered through a small needle (eg. 16 g-18 g); able to be detected using a handheld probe using relatively high frequencies (>1 kHz), able to provide a substantially uniform response from any detection direction, and robust for implantation and surgical removal, together with a system that is able to distinguish the lesion marker from other magnetically responsive materials. The present invention aims to address this need.

SUMMARY OF THE INVENTION

According to a first aspect of the present invention there is provided a detection system for locating a marker, the system comprising:

at least one implantable marker, the implantable marker comprising at least one piece of magnetic material that exhibits a large Barkhausen jump (LBJ) in its magnetisation curve;

at least one drive coil arranged to excite the marker with an alternating magnetic field and at least one sense coil arranged to detect a signal received from the excited marker, a magnetic field generator arranged to drive an alternating magnetic field through the at least one drive coil; and at least one detector arranged to receive the signal from the sense coil and detect one or more harmonics of the drive frequency in the received signal, wherein the at least one drive coil excites the marker below the switching field required to initiate bistable switching behaviour of the LBJ material of the marker.

Large Barkhausen Jump materials, also known as a LBJ material, a bistable switching material or a material with large discontinuous changes in its magnetisation curve, undergo a rapid reversal of their magnetic polarization ("bistable switching" behaviour) when excited by an external magnetic field whose field strength opposing the instantaneous polarization of the material exceeds a predetermined threshold value, the switching field $H_{SW}$. In the present invention, the marker utilises a "sub-bistable" mode of excitation for its LBJ material that causes a measurable harmonic response to be sensed even when the excitation field is below that of the 'switching field'.

Generally, this bistable switching behaviour also requires a length of material of a critical length. The implantable marker of the detection system is preferably provided below the critical length required for this rapid reversal, generally being <25 mm, more preferably <10 mm, especially <5 mm, this being preferable in order to reduce the size of the marker for convenient implantation and marking of smaller lesions. The marker utilises the "sub-bistable" mode of excitation for its LBJ material that causes a measurable harmonic response to be sensed even when the length of the LBJ material is below its 'critical length' for reaching the bistable mode.

Preferably, the marker comprises less than 5 mg of LBJ material in order that the amount of material implanted in the body is minimised. The material may be provided in the form of a wire. Examples of such materials include, but are not limited to, iron-, cobalt- and nickel-rich glass-coated amorphous microwires, iron-silicon-boron based amorphous microwires, iron-cobalt based amorphous microwires, and/or bulk metallic glass wires, but any material in which a LBJ response can be excited may be suitable. The wires may be coated and/or provided within a hollow tube and/or may be deployable from an initial compact configuration to an extended, deployed configuration. Preferably, the marker is deployable from a needle having an inner diameter of less than 2 mm in order to minimize the trauma and pain associated with implanting the marker.

The marker for use in the present invention is preferably configured such that when implanted into the body the magnitude of a harmonic response from the marker when interrogated by an alternating magnetic field is substantially the same when measured from any direction relative to the marker, that is the marker provides a similar magnetic dipole length in any direction of sensing so as to provide a uniform magnetic response and allow the distance between the probe and the marker to be determined. Preferably, the marker comprises a wireform shape with a magnetic dipole length of at least 50% of the maximum dimension of the deployed marker.

A uniform harmonic response from any direction of the marker may be achieved by a number of different geometries of marker. For example, the marker may comprise lengths of the LBJ magnetic material provided along three orthogonal axes x, y and z. The marker may be bent into different conformations to provide lengths of material in each direction or may have separate lengths joined together. Preferably, the angle between the different lengths is 60°-120°, more preferably 90-110°. In an embodiment wherein the marker is deployable from an initial compact configuration to an extended, deployed configuration, it is the latter configuration that should provide the uniform harmonic response from any direction.

The detection system preferably comprises an output module for processing the received harmonic signal and providing at least one indicator to the user relating to a location of the marker relative to the sense coil, for example an indication of the proximity, distance, direction or orientation of the marker with respect to the sense coil.

More preferably, the system processes one or more aspects of the harmonic response of the marker, such as the magnitude of one or more odd harmonics (eg, $3^{rd}$ and $5^{th}$), even harmonics (eg. $2^{nd}$, $4^{th}$ and $6^{th}$) or a combination of both or the ratios of these harmonics to each other or the fundamental frequency. Appropriate filters may be provided to enhance the sensed signals.

The output module may include a visual display or sound generator.

In a preferred embodiment of this aspect of the invention, both the drive and sense coils are provided in a handheld probe to simplify the setting up of the system for the user.

Alternatively, only the sense coil may be provided in a handheld probe. In this embodiment, a larger drive coil may be provided external to the probe to enable an increased magnetic field to be generated at the marker site. For example, the drive coil may be provided within a pad for placement near or beneath a patient.

According to a second aspect of the present invention there is provided a method of detecting an implantable marker, the implantable marker comprising at least one piece of magnetic material that exhibits a large Barkhausen jump (LBJ) in its magnetisation curve, the method comprising applying an alternating magnetic field to the marker to excite the marker, the field being of a magnitude below the switching field required to initiate bistable switching behaviour of the LBJ material of the marker; and detecting one or more harmonics of the drive frequency of a signal received from the excited marker caused by a change in magnetization of the marker below its switching field.

The application of the alternating magnetic field to excite the marker below the switching field results in a sub-bistable response being detected for the marker.

Preferably, the drive frequency is above 1 kHz, preferably being in the range 1-100 kHz, especially 10-40 kHz.

The method preferably includes measuring an aspect of the harmonic response of the marker to provide an output relating to the location of the marker. For example, this may be the amplitude of one or more odd harmonics, even harmonics or a combination of both, the ratios of these harmonics to each other or to the fundamental frequency. Appropriate filtering and processing of the signals may be provided to enhance the output provided by the method.

A number of markers of different lengths and/or geometries may be used in the method such that the harmonic response of each of the markers can be distinguished from the others.

BRIEF DESCRIPTION OF THE DRAWINGS

For a better understanding of the present invention and to show more clearly how it may be carried into effect, reference will now be made by way of example only, to the accompanying drawings, in which:

FIGS. 9A to 9I illustrate various configurations for a marker for use with the present invention;

DETAILED DESCRIPTION OF THE INVENTION

The present invention relates to a magnetic marker that can be implanted for marking a target site in the body, and subsequently be detected and localised using a handheld probe. The invention provides a detection system and method for locating the position of the implanted marker in the body.

The marker may be implanted in a site requiring marking in the body. This may, for example, be a tumour or other lesion or site of interest in soft tissue. Examples include but are not limited to benign lesions, cancerous lesions and lymph nodes. The marker may be placed in or near a lesion or multiple markers may be placed to mark the margins or perimeter of a surgical site, for example the margins of a soft tissue sarcoma.

The detection system and method of the present invention utilises a different mode of excitation for LBJ materials that has not prior hereto been recognised. The inventors have surprisingly found that a different mode of excitation for LBJ materials incorporated into a marker produces a measurable harmonic response even when the length of wire is below the 'critical length' and the excitation field is below the 'switching field'. The concepts of 'critical length' and 'switching field' for LBJ wires are known from for example Vazquez (A soft magnetic wire for sensor applications., J. Phys. D: Appl. Phys. 29 (1996) 939-949). Furthermore, the effect measured in the invention increases in magnitude at higher excitation frequencies and can be operated at frequencies far higher than 3 kHz. This realisation has enabled a new type of detection system to be provided that has superior properties to previous systems that used implantable magnetic markers for marking the site of a lesion.

The present invention is based on the inventors' realization and utilization of a previously unidentified "sub-bistable" behaviour in addition to the known bistable behaviour of LBJ materials.

Figure 1A:
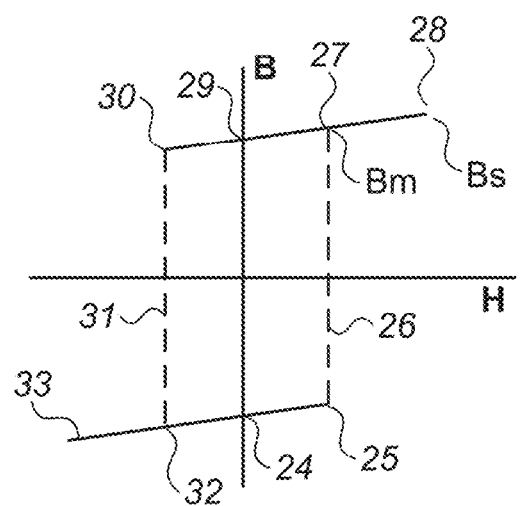
FIG. 1A is a magnetization curve for a LBJ wire according to the prior art.
Figure 1B:
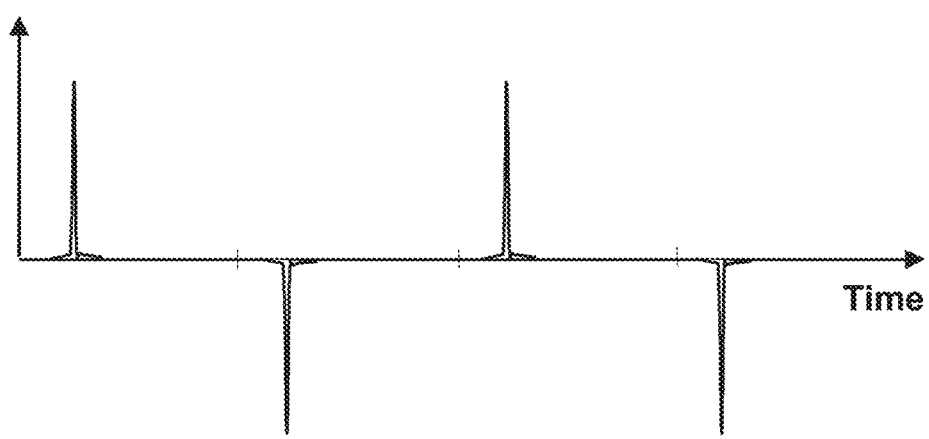
FIG. 1B is the time domain response of the LBJ wire of FIG. 1A when excited by a sinusoidal field.

The magnetisation curve in FIG. 1A is for a prior art LBJ wire (U.S. Pat. No. 4,660,025). This shows the characteristic reversal of magnetisation once the switching field indicated by '25' is exceeded. When excited by a sufficiently high field, the characteristic pulses are seen in the time domain (see FIG. 1B). The pulses are sometimes reported as superimposed onto a sine wave, which can be seen when the drive signal is not being filtered out fully. According to the magnetisation curve, an excitation field, H, lower than the switching field 25 will result in little or no change to the magnetisation, B, except the effect of moving from '24' to '25', a small change in magnitude, but no change in polarity of B.

Figure 3:
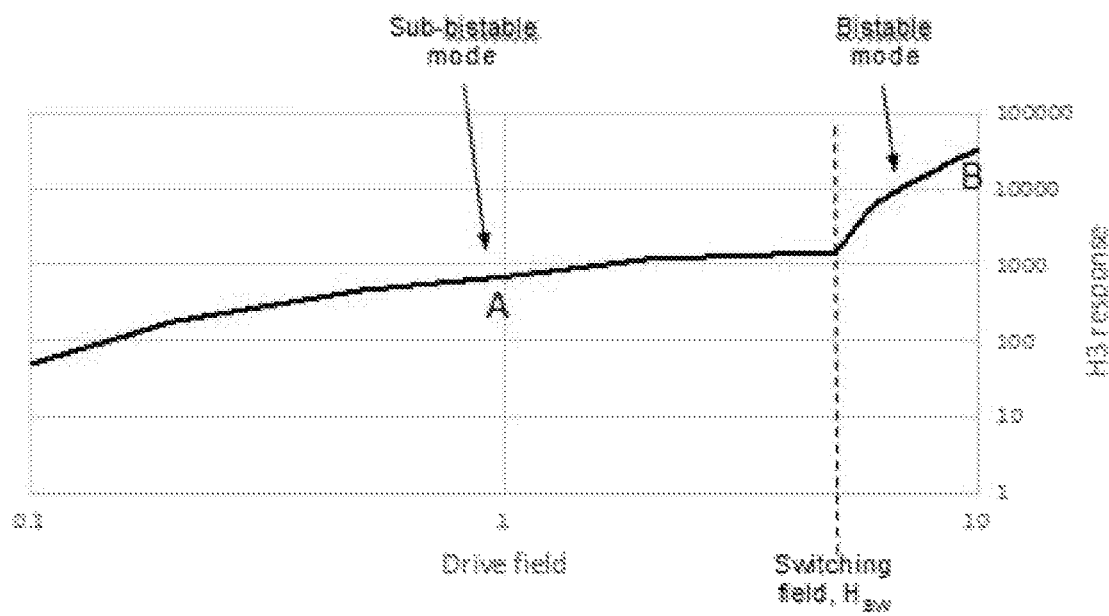
FIGS. 3 and 3A illustrate a third harmonic (H3) response (arbitrary units) from an LBJ wire as the magnitude of the 100 Hz excitation field is increased, shown respectively with both log-log and log-linear scales.
Figure 3A:
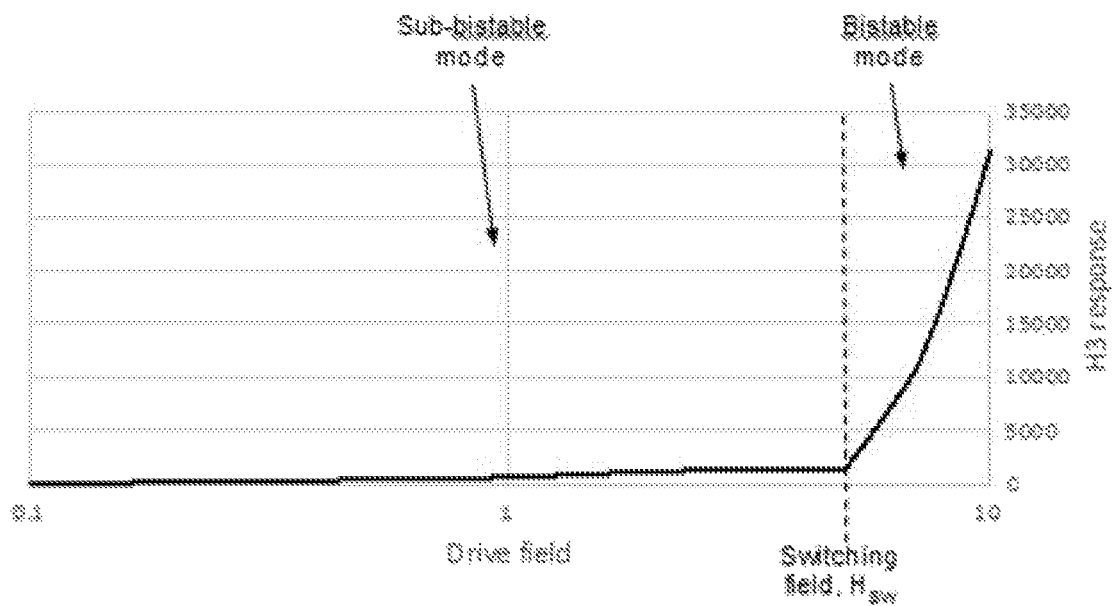

The inventors have found that this curve does not fully describe the behaviour of the LBJ material when placed in an alternating magnetic field. For example, when a piece of cobalt-iron amorphous LBJ microwire above the critical length is excited with an alternating magnetic field at 100 Hz according to the arrangement in FIG. 1A, the third harmonic (H3) response is shown in FIGS. 3 and 3A. H3 is here taken as representative of the harmonic content of the marker response. Once an H3 response is distinguishable from noise, it increases in an approximately linear relationship with excitation field. This continues until the switching field is reached, at which point the response increases dramatically in magnitude as the bistable switching is initiated. It is this point at which LBJ wire of length above a critical length is normally identifiable. The log-linear and log-log scales clearly illustrates the change in mode. However, FIGS. 3 and 3A show that by using the "sub-bistable" mode, the marker can be detected even when the field is almost 2 orders of magnitude lower than the switching field required for bistable behaviour. This means that for a given drive field, the marker can be detected at a much greater distance from the probe.

Figure 2:
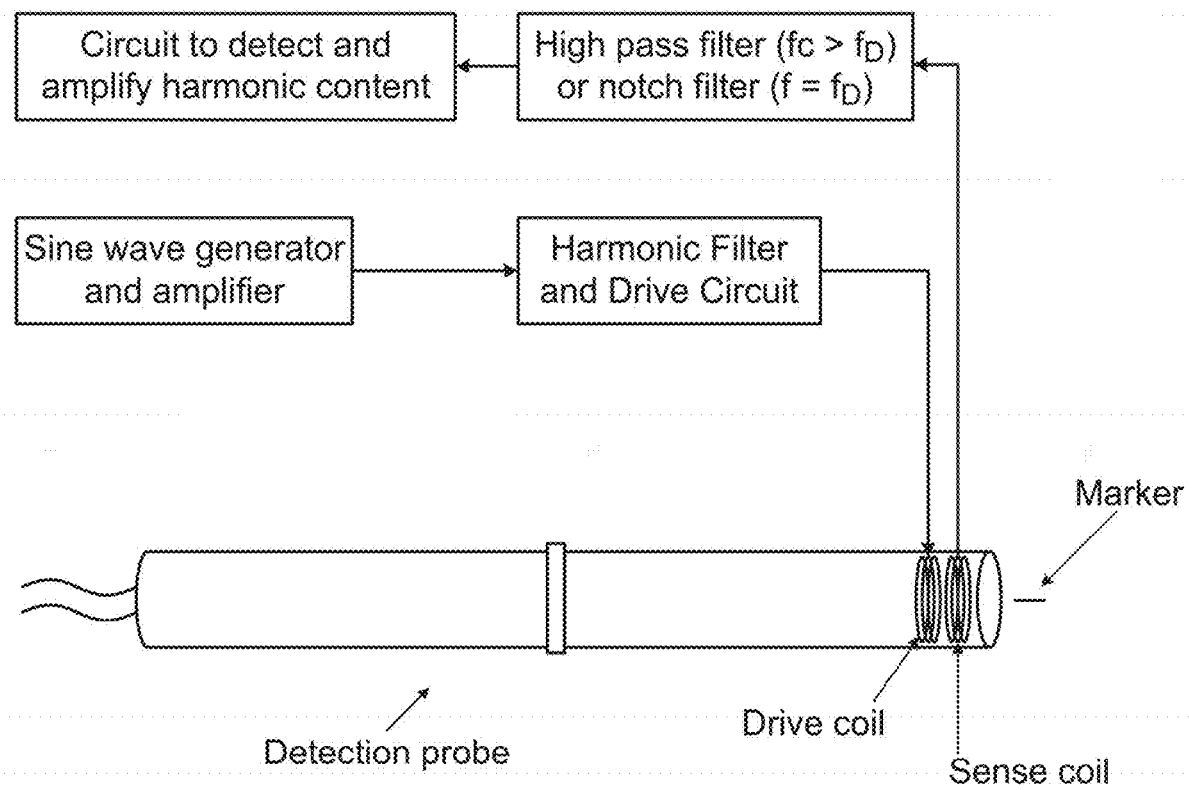
FIG. 2 illustrates the components used to investigate the sub-bistable and bistable behaviour for a LBJ wire with excitation fields of different magnitude.

FIG. 2 illustrates the components used to investigate the sub-bistable and bistable behaviour for a LBJ wire with excitation fields of different magnitude. FIGS. 3 and 3A illustrates the third harmonic (H3) response (arbitrary units) from an LBJ wire as the magnitude of the 100 Hz excitation field is increased, shown with both log-log (FIG. 3) and log-linear scales (FIG. 3A).

Figure 3B:
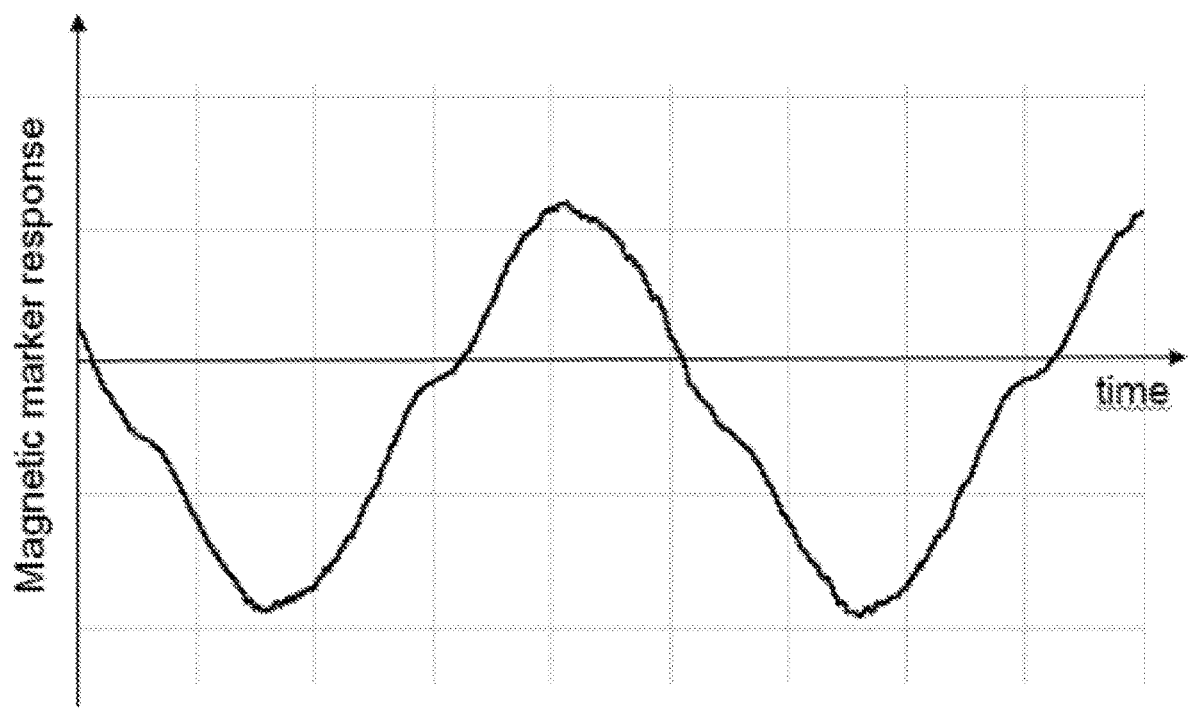
FIG. 3B shows the time-domain response in the sub-bistable region at point A in the top graph of FIG. 3 when driven by a sinusoidal wave.
Figure 3C:
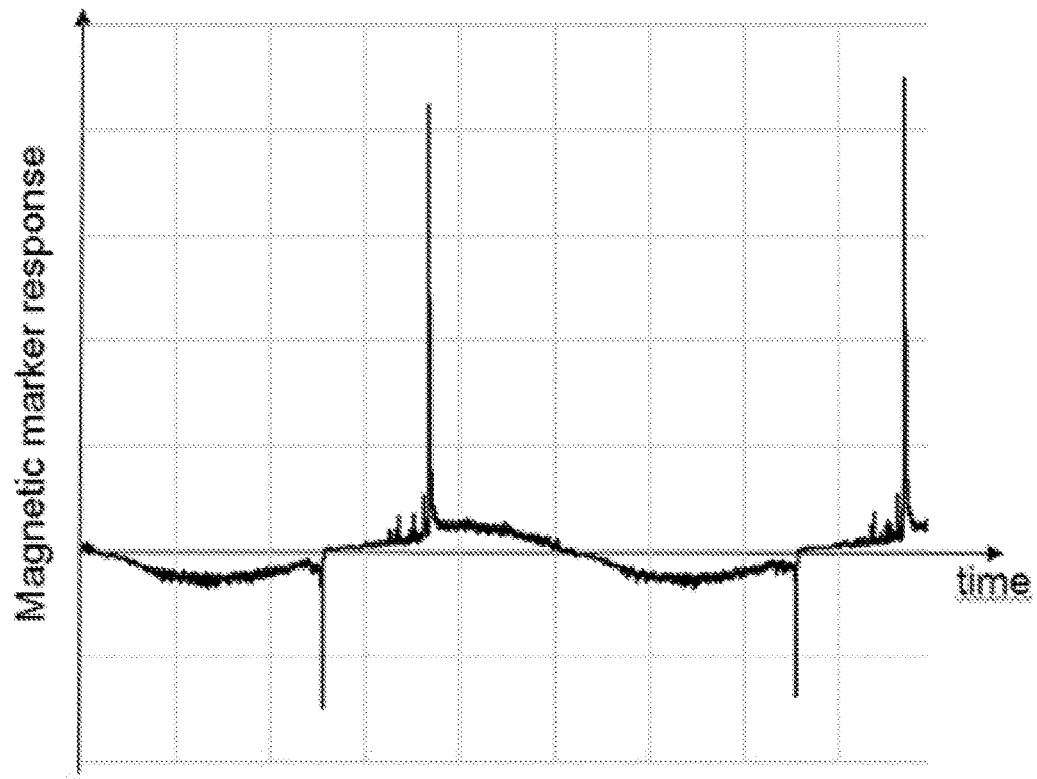
FIG. 3C shows the time-domain response in the bistable region at point B in the graph of FIG. 3 when driven by a sinusoidal wave.
Figure 3D:
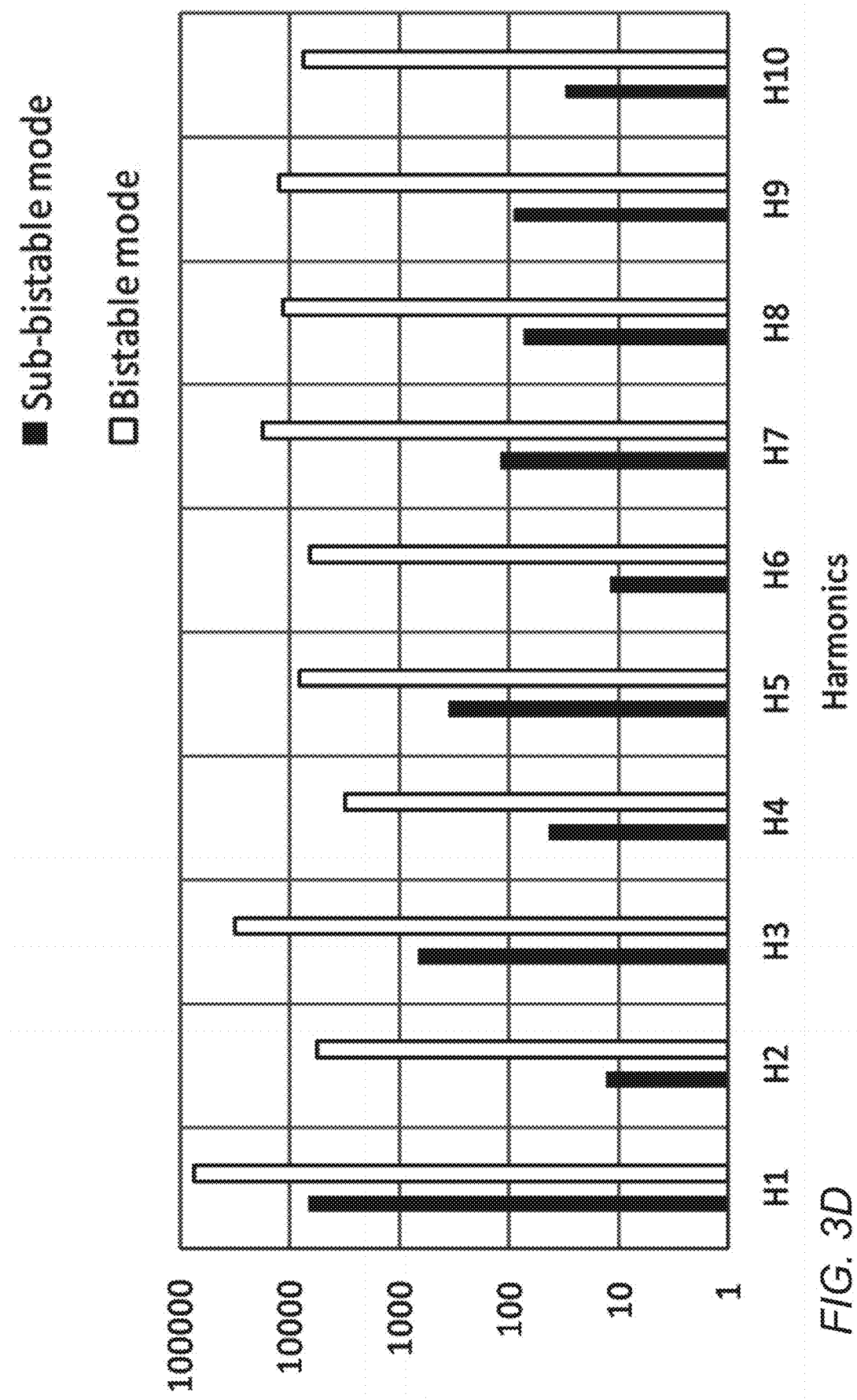
FIG. 3D is the Frequency domain response from an LBJ wire in the sub-bistable and bistable switching modes at 100 Hz excitation frequency.

FIG. 3B shows the time-domain response in the sub-bistable region when driven by a sinusoidal wave. It is seen as a distorted sine wave, in contrast to the bistable time-domain response which shows the classic short pulses as the magnetisation reverses (see FIG. 3C). In the frequency domain, the rich harmonics of the bistable mode seen in the prior art contrast with the less rich harmonic response of the sub-bistable mode (see FIG. 3D). However, such harmonic response is still richer than the response from non-bistable amorphous wires and the inventors have surprisingly found that this response may be used to accurately identify a marker even when the length of wire is below the 'critical length' and the excitation field is below the 'switching field'.

Figure 4:
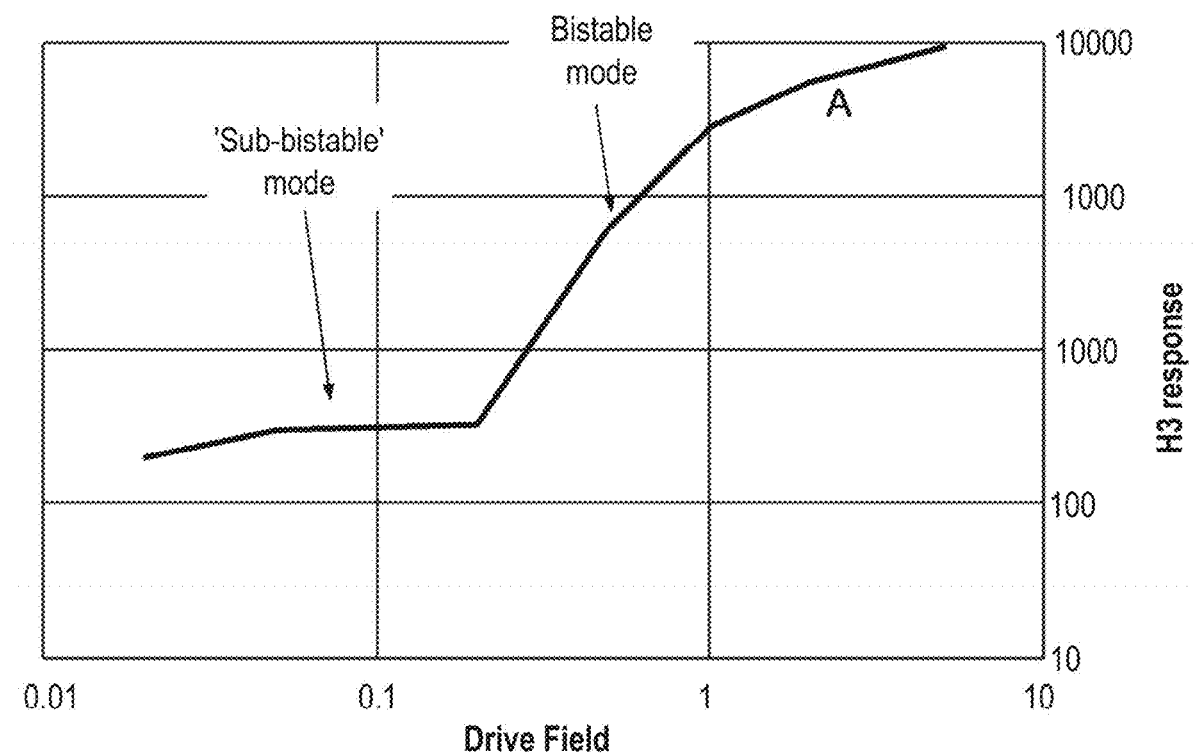
FIG. 4 is the Frequency domain response from an alternative LBJ wire in the sub-bistable and bistable switching modes at 10 kHz excitation frequency, and time domain response for the same wire at position A in the frequency domain curve.
Figure 4:
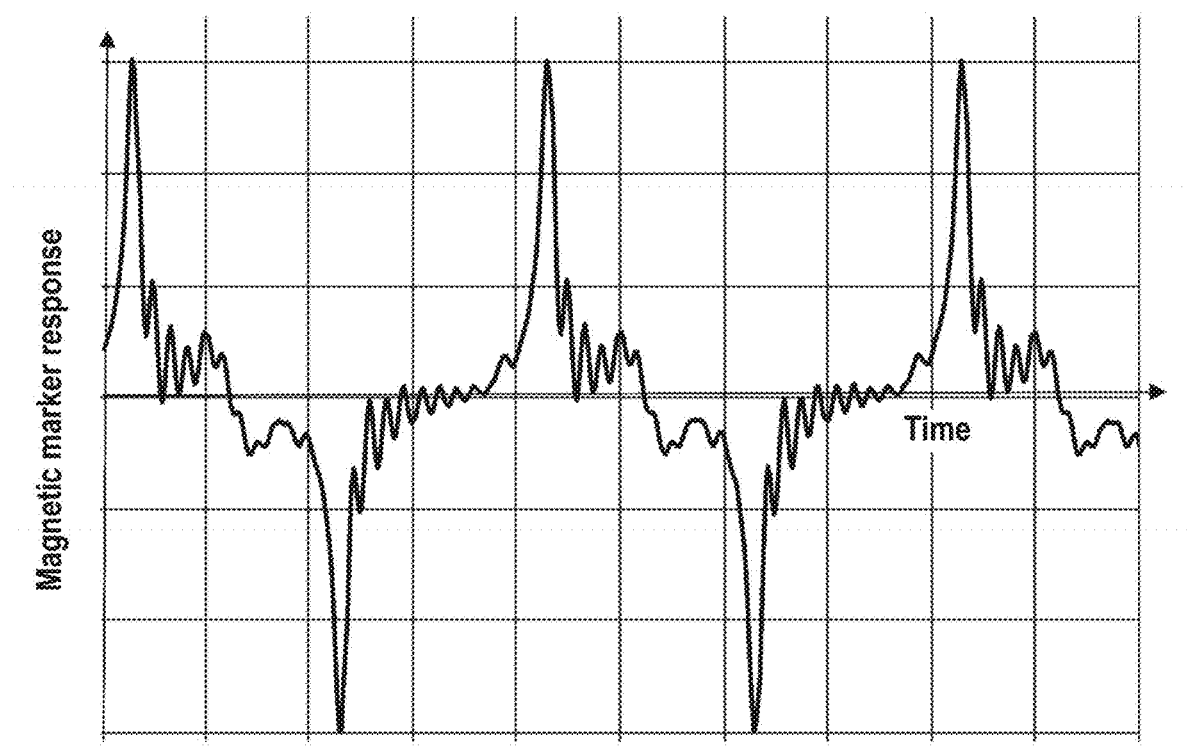

Similar behaviour was also observed for other LBJ wires, including glass coated microwires that have critical lengths of a few millimeters. FIG. 4 shows the frequency domain response from another LBJ wire in the "sub-bistable" and bistable switching modes at 10 kHz excitation frequency, and time domain response for the same wire at position A in the frequency domain curve. The wire is a 3 mm long glass coated microwire (inner diameter 15 um, outer diameter 32 um) excited at 10 kHz using the same experimental arrangement of FIG. 2.

Figure 5:
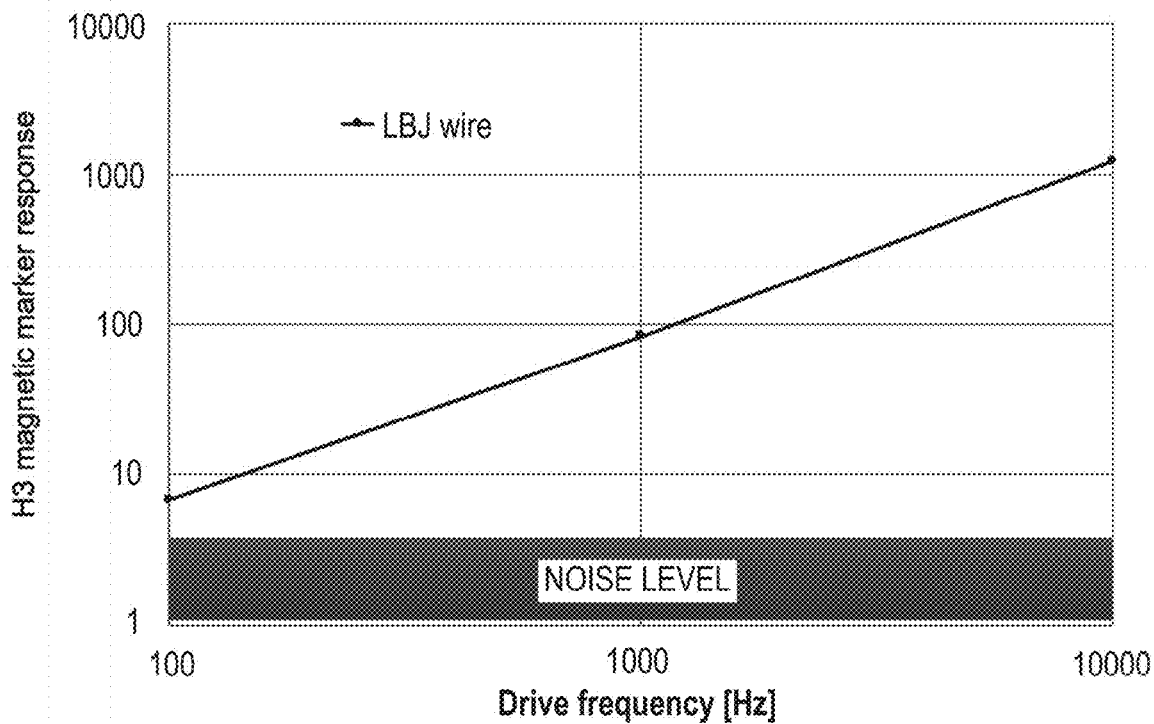
FIG. 5 illustrates the third harmonic response from a cobalt-iron amorphous LBJ microwire where the critical length of the material is approximately 40 mm, and the length of the marker is 3 mm, showing the response increasing as the frequency of the excitation field is increased.

A similar "sub-bistable" response is also seen with a wire that is shorter than the critical length. For example, FIG. 5 shows the response from a piece of cobalt-iron amorphous LBJ microwire where the critical length of the material is approximately 40 mm, and the length of the microwire in the marker is 3 mm. The marker is therefore too small to exhibit bistable behaviour. However, it does show the sub-bistable harmonic response and the magnitude of the H3 response increases with increasing frequency up to at least 10 kHz.

Figure 6A:
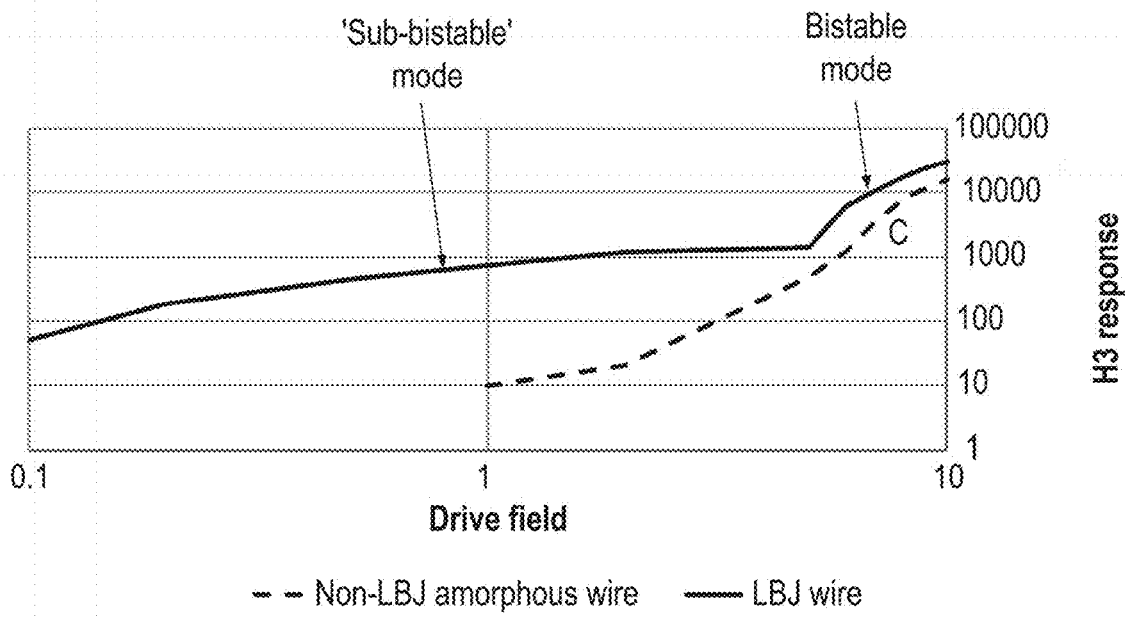
FIG. 6A shows a third harmonic (H3) response from a normal amorphous metal wire compared with a LBJ wire as excitation field is increased at 100 Hz.

It is known in the art that a number of ferrous and amorphous magnetic materials that do not have a LBJ magnetisation curve can produce a harmonic response if excited with a sufficiently high field. However, the sub-bistable effect identified herein is not seen with the 'non-LBJ' materials. Accordingly, it is a requirement of the present invention for the marker to contain at least some LBJ material. FIG. 6A compares the LBJ wire shown in FIG. 3A with a similar shaped amorphous metal wire that does not have a LBJ in its magnetisation curve. Here, the response at low fields is one to two orders of magnitude smaller than the sub-bistable response from the LBJ wire. In addition, the sharp change in behaviour at the switching field is not seen with the non-LBJ wire, and at lower drive fields, the response is too small to be distinguished from noise. This would limit the ability of a marker to be detected at a distance from the probe.

Figure 6B:
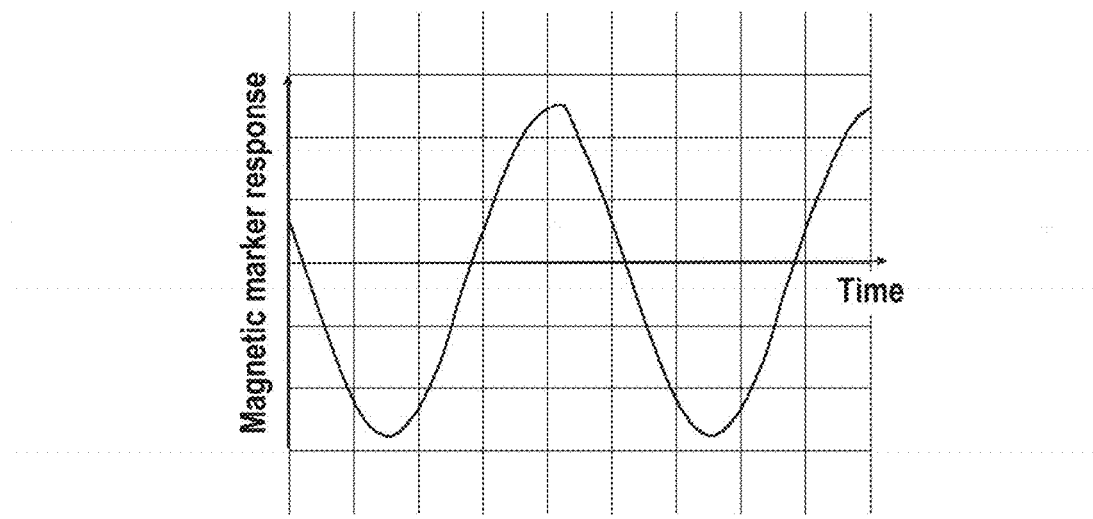
FIG. 6B shows the time domain response from the non-LBJ normal amorphous metal wire at point C in the graph of FIG. 6A.

The time-domain response seen at point C in FIG. 6A is shown in FIG. 6B. There is clearly no bistable behaviour nor are the characteristic pulses of FIG. 3C seen.

Thus the present invention requires an implantable magnetic marker comprising at least one piece of a large Barkhausen jump material (LBJ) which is deployed to mark a tissue site in the body for subsequent surgery, and a magnetic detection system including a drive coil to excite the marker. The system is characterised in that when the drive coil excites the marker with an alternating magnetic field below the switching field for bistable switching of the marker, a harmonic response is generated that allows the marker to be detected and localised.

Figure 7:
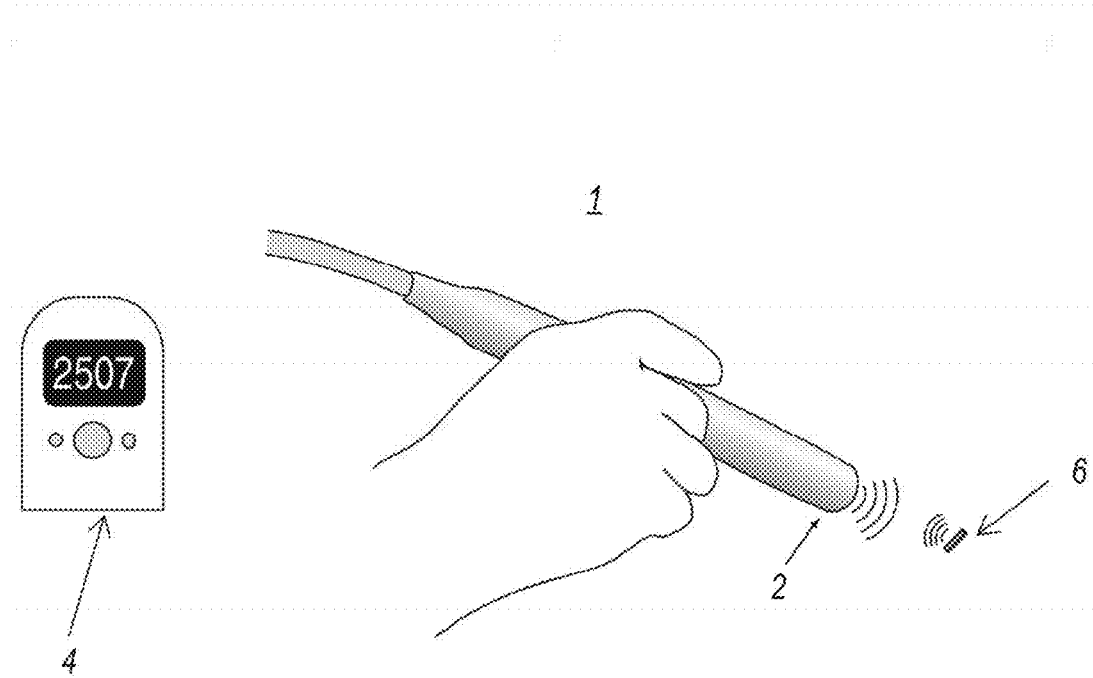
FIG. 7 is a schematic diagram of an embodiment of a detection system according to the present invention.

FIG. 7 of the accompanying drawings shows a schematic diagram of an embodiment of a detection system and marker according to the present invention. The detection system 1 comprises a probe 2 connected to a base unit 4. The probe has one or more drive coils that generate an alternating magnetic field to excite a magnetic marker 6. The marker comprises at least one piece of magnetic marker material having a large Barkhausen discontinuity in its magnetisation curve, also known as a large Barkhausen jump material, a LBJ material, a bistable switching material or a material with large discontinuous changes in its magnetisation curve. When the LBJ material is exposed to an external magnetic field whose field strength opposing the instantaneous magnetic polarization of said length of material exceeds a predetermined threshold value, the switching field $H_{SW}$, its magnetic polarization undergoes a rapid reversal. This reversal of magnetisation generates a magnetic pulse with rich harmonic components. Conventionally, the markers are sized to be above the so-called 'critical length', that is the length at which the magnetization can undergo the full bistable transition or 'flipping' behaviour which is required to generate a significant harmonic response. However, the present inventors have found that a harmonic response can be obtained from markers significantly below their critical length and/or below the switching field $H_{SW}$ and this is advantageous for use for localization of the implantable marker.

The harmonic approach also allows detection of the marker whilst being relatively impervious to sources of noise at the fundamental frequency such as stray fields, diamagnetic response from tissue, and Eddy currents.

The probe 2 of the detection system further contains one or more sense coils arranged to detect the changes in the magnetic field caused by the change in magnetisation of the marker.

To detect markers in any typical lesion or site of interest the probe must have a detection depth of at least 30 mm, preferably more than 40 mm and more preferably more than 50 mm. Ideally the probe gives the same magnitude of response regardless of the direction in which the marker is approached. This is to provide consistent feedback to a surgeon on the location of the marker relative to the probe.

Figure 8:
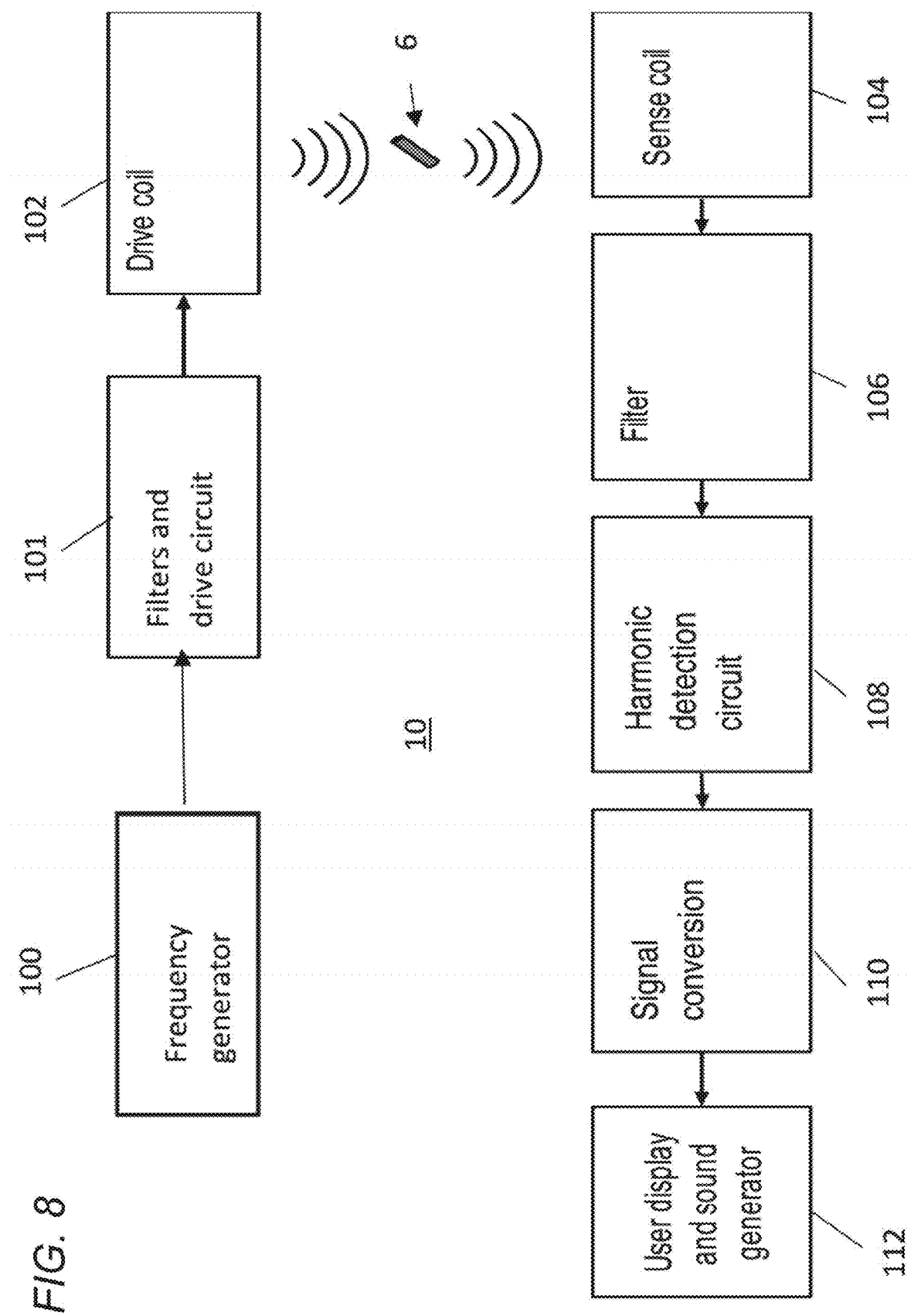
FIG. 8 is a block diagram of a magnetic detection system according to an embodiment of the present invention.

FIG. 8 of the accompanying drawings shows a block diagram of a magnetic detection system 10 according to an embodiment of the present invention. A frequency generator 100 for example an oscillator or waveform generator ($f_D$ is 0.5 to 30 kHz) generates a preferably sinusoidal alternating signal which excites one or more drive coils 102. A sinusoidal signal minimises the harmonic components in the drive field such that the sense coil detects no spurious harmonic signals. The one or more drive coils generate an alternating magnetic field that extends into the tissue containing a magnetic marker 6 comprising at least one piece of a large Barkhausen jump material (LBJ).

The alternating magnetic field excites the marker 6 and the magnetisation of the marker leads to the generation of harmonic components in the field. Depending on the arrangement of the marker, the harmonics may be odd harmonics, ($3^{rd}$, $5^{th}$, $7^{th}$ etc.) or even harmonics ($2^{nd}$, $4^{th}$, $6^{th}$ etc.) or a combination of both odd and even harmonics. The marker is detected by measuring the magnitude of one or more of the harmonic frequencies directly or by measuring the ratio of the magnitude of one or more harmonics to others or to the magnitude of the fundamental frequency.

The response from the marker is detected by one or more sense coils 104 to generate a sense voltage or current. Preferably the sense coils are in a handheld or robotic probe. A high-pass or notch filter 106 may be arranged to filter out or attenuate at least components of the sense signal at the drive frequency so that the resulting signal has minimal content at the drive frequency and comprises higher harmonic components of the signal, for example the second, third, fourth, fifth or seventh order harmonics or combinations of these. The filter may take the form of a passive LCR type filter comprising a known arrangement of for example capacitors, inductors and resistors or an active filter comprising a known arrangement for example based on one or more op-amps.

The filtered signal may be fed to a harmonic detection circuit 108 which amplifies one or more harmonic components of the signal and converts the signal 110 to a measure of distance from the probe to the marker. A user display and sound generator 112 provides a visual and audio output to the user indicating for example, the proximity of the marker or the magnitude of the magnetic signal. The system may indicate the proximity, size, distance to, direction or orientation of the marker, or combinations of these.

The drive signal from drive coils 102 may be electronically filtered by filters 101 to attenuate any harmonic parts of the drive signal so that the alternating magnetic field is primarily at the desired excitation or drive frequency. This helps to avoid spurious responses at higher frequencies that could be erroneously interpreted as harmonic responses. If desired, more than one drive frequency may be added to create a more complex magnetic signal, either by superposition/modulation or by multiplexing the signals so that a different frequency is generated at different times.

The drive frequency may be in the range 100 Hz to 100 kHz. Higher frequencies towards 100 kHz are advantageous to maximise the sensed signal (see FIG. 1g). A higher frequency also allows more cycles per second to be averaged during detection to improve noise suppression while still delivering a 'real time' output to the user i.e. updating the output signal at least 10 times per second. Hence for noise suppression a frequency of at least 1000 Hz and preferably at least 10 kHz is desirable. In order to give an apparent 'real time' response to the user, the output needs to be updated at least every 0.1 s. A frequency of 1 kHz allows 100 cycles to be averaged between each update to the user, and 10 kHz allows 1000 cycles to be averaged between each update to the user.

Advantages can also be gained from a lower drive frequency, and these include reduced eddy current losses both in the marker (in cases where it is prone to eddy currents for example if it has high conductivity) and from the surrounding tissue. For reduced eddy current losses, a frequency of less than 30 kHz is advantageous. Also, in the operating room environment, electromagnetic interference signals are more frequently experienced at frequencies above 100 kHz and therefore choosing a drive frequency such that the harmonics of interest are less than 100 kHz may be beneficial.

As mentioned above, the markers of the detection system according to the first aspect of the invention each comprise one or more lengths of material ("magnetic marker material") which gives a harmonic or non-linear response to an alternating magnetic field produced by a large Barkhausen discontinuity in the magnetisation curve. Examples of such materials include iron-, cobalt- and nickel-rich glass-coated amorphous microwires, iron-silicon-boron based amorphous microwires, iron-cobalt based amorphous microwires, and bulk metallic glass wires.

The examples of the marker illustrated in FIGS. 9A to 9H are arranged such that the harmonic response to an alternating magnetic field is more uniform from any given direction than that of, for example, a single straight length of marker material, thus providing a marker that may be more easily located by a surgeon using a probe.

In FIG. 9A, the marker 6 comprises a length of magnetic marker material bent to describe three or four edges 6a, 6b, 6c of a tetrahedron. By so doing, the harmonic signal response of the marker is more uniform from any given direction of sensing. In a further aspect, the radii of the bends 6d may be larger to allow the marker to be packed into an outer tube more easily prior to deployment.

In FIG. 9B, the marker comprises a length of magnetic marker material bent into a portion of a circle 6e, with one end 6f bent radially towards the centre and then bent substantially at 90° to form a portion 6 g along the axis of the circle.

In FIG. 9C, the marker 6 comprises lengths of magnetic marker material arranged along three orthogonal axes x, y and z to form the shape of a 'jack'.

In FIG. 9D, the marker comprises a length of magnetic marker material with a straight central section 6h and two further sections 6i, 6j, one at each end bent orthogonally from each other and the central section. In a further aspect, the radii of the bends 6k may be larger to allow the marker to be inserted into an outer tube more easily.

Figure 9E:
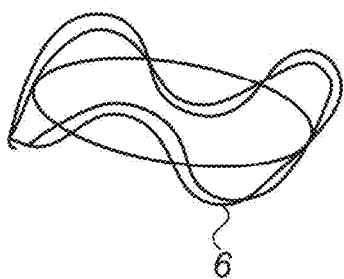

In FIG. 9E the marker 6 comprises a length of magnetic marker material in the shape of a circular standing wave, i.e. formed into a uniform wave shape and then bent round to join the ends and form a circle in plan view.

Figure 9F:
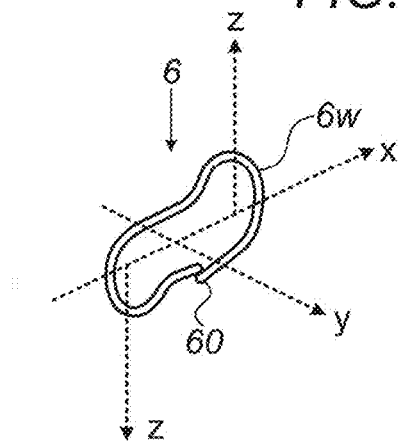

In FIG. 9F, the marker comprises an elliptical or oval shaped length of magnetic marker material 6n with the wire ends 6o joined or close to one another but not joined. Two portions of the ellipse or oval at the ends of its longer axis are bent to approximately 90° of the plane of the ellipse. The bent portions comprise approximately one quarter to one third of the area of the ellipse or oval.

Figure 9G:
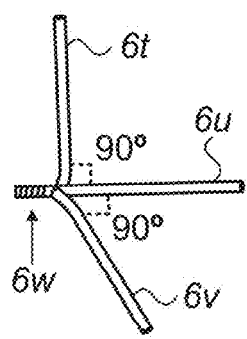

In FIG. 9G, the marker comprises three lengths of magnetic marker material 6t,6u,6v arranged orthogonally to each other to form substantially an orthogonal tripod or the vertex of a cuboid. The three lengths are joined with a joining section 6w that allows the lengths to lie parallel to each other prior to deployment and then redeploy to form an orthogonal tripod.

Figure 9H:
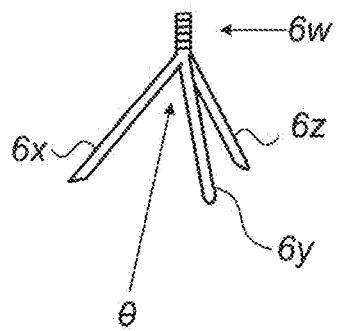

In FIG. 9H, the marker comprises three lengths of magnetic marker material 6x,6y,6z arranged to form a tripod with a non-orthogonal angle between the legs of the tripod. The three lengths are joined with a joining section 6w that allows the lengths to lie parallel to each other prior to deployment and then redeploy to form the tripod.

Figure 9I:
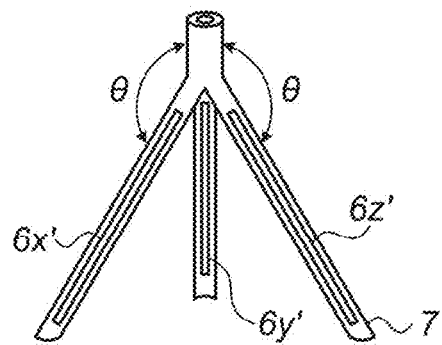

In FIG. 9I, the marker comprises three lengths of magnetic material 6x', 6y', 6z', within their own biocompatible barrier 7. The tripod has been constructed from a tube, complete at the top, with three partial shell legs forming a tripod within which the three lengths are held.

Preferably the angle between the legs is chosen such that the harmonic magnetic response is as uniform as possible from any direction. For example, tripods formed from three 5 mm lengths of cobalt-iron amorphous LBJ microwire are shown in the table below. The tripod is uniform with three equally spaced legs, but the angle between the legs is varied, while being tested using the arrangement of FIG. 2.

Figure 10:
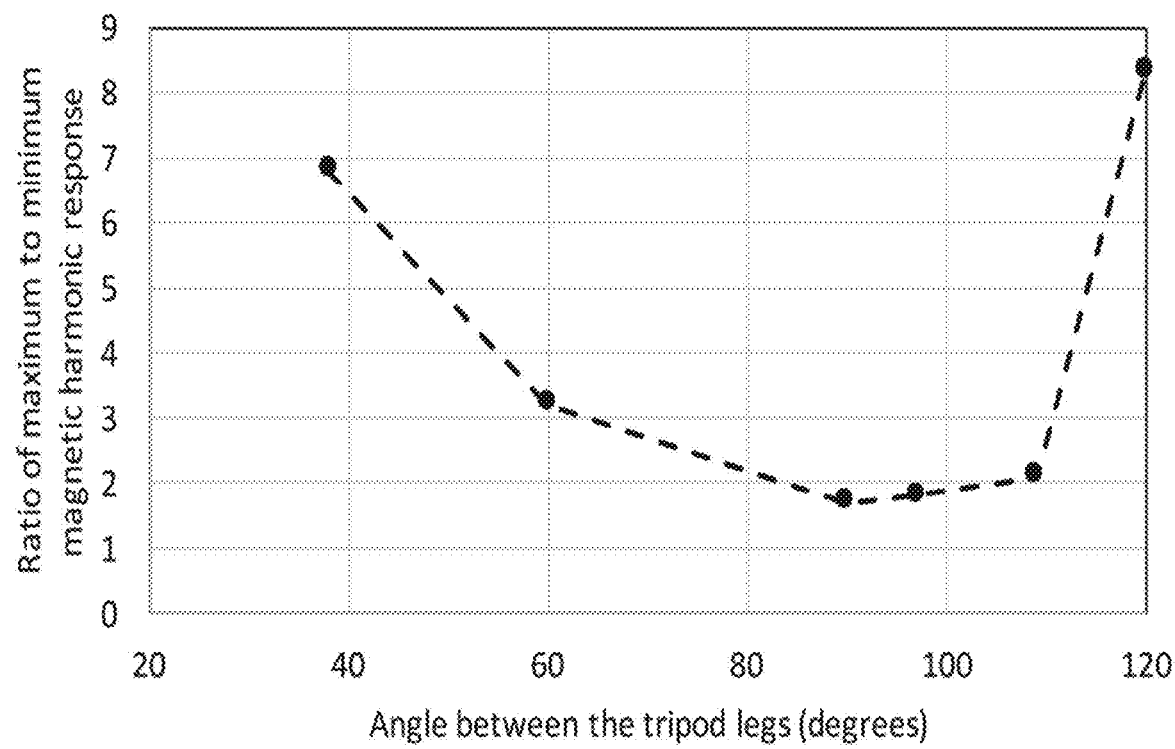
FIG. 10 demonstrates the variation of the ratio of maximum to minimum magnetic marker response with the angle between the tripod legs for the marker of FIG. 9H.

Table 1 below and FIG. 10 demonstrates how the ratio of maximum to minimum magnetic harmonic response from the marker of FIG. 9H varies with the included angle ø between the legs. An ideally uniform response would be indicated by a ratio of 1. The table and figure shows the variation of the ratio of maximum to minimum magnetic marker response with the angle between the tripod legs for the marker of FIG. 9H. The figure shows that the uniformity of the response is optimal when the angle between the legs is in the range 60° to 110°, and more preferably when the angle is between 90° and 120°.

TABLE 1

| Angle between the tripod legs, ø | Ratio of maximum to minimum H3 response (at a distance of 20 mm) |
|---|---|
| 38° | 6.8 |
| 60° | 3.2 |
| 90° | 1.7 |
| 97° | 2.0 |
| 109° | 2.1 |
| 120° | 8.3 |

The length or lengths of magnetic marker material (formed from a material with a large Barkhausen discontinuity in its magnetisation curve) in the examples described herein may comprise any of the following forms:
  a) a length of solid wire;
  b) a glass-coated microwire with core diameter between 5 and 100 micrometres and a coating thickness of between 0.5 and 40 micrometres;
  c) a bundle of lengths of solid wire or glass-coated microwire; or
  d) a hollow tube;

Any of the markers of FIG. 9A-9I may comprise more than one piece of magnetic marker material together with additional material to join or enclose the pieces of magnetic marker material and form the final shape of the marker. The marker may comprise a tube, tubes or a complete or partial shell of another material within which the lengths of magnetic material of the marker are held. The magnetic material may also be coated or enclosed within a further biocompatible material.

The shell may also function to assist in the deployment of the marker from an initial shape and configuration when it is inside the deployment device, to a final position once the marker has left the deployment device and is in the tissue. For example, the tube or tubes or shell containing the magnetic marker material may comprise a biocompatible shape memory alloy such as a Nitinol alloy, the alloy being manufactured such that on leaving the deployment device and being exposed to body temperature the material performs a shape transition and reconfigures from a pre-deployed shape that can fit within a narrow gauge needle e.g. 14 g-18 g to a final deployed shape as described for example in any of FIGS. 9A to 9I.

In a further example, the tube or tubes containing the magnetic marker material comprises a biocompatible resiliently deformable material such as a superplastic Nitinol alloy or spring material, such that when it is deployed in the body it resiliently reconfigures through for example the elasticity of the material from a pre-deployed shape that can fit within a narrow gauge needle e.g. 14 g-18 g to a final deployed shape as described for example in any of FIGS. 9A to 9I.

Figure 12A:
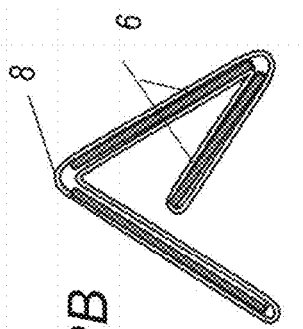
FIGS. 12A to 12E illustrate markers according to FIG. 9A together with a deployment system.
Figure 12B:
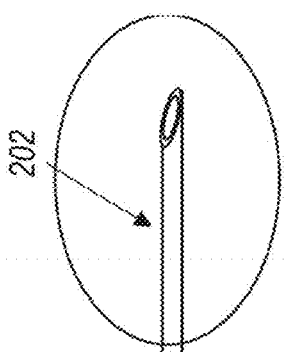
Figure 12C:
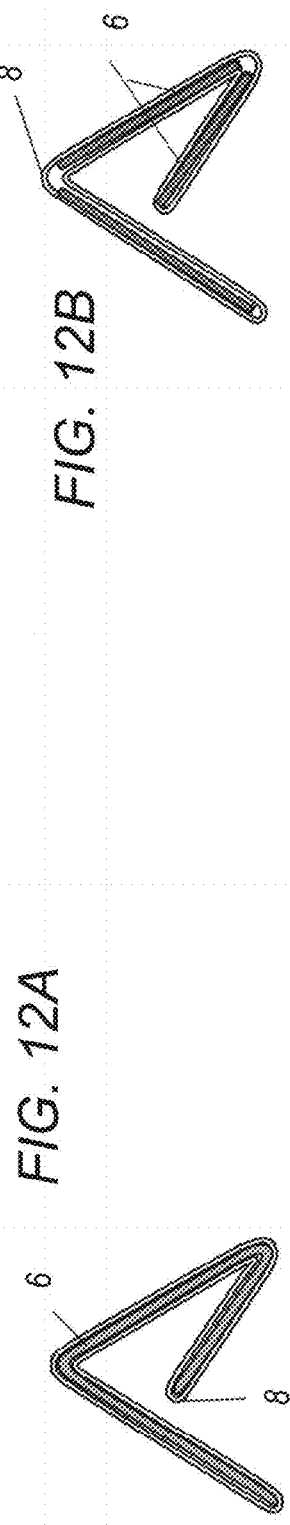
Figure 12D:
Figure 12E:
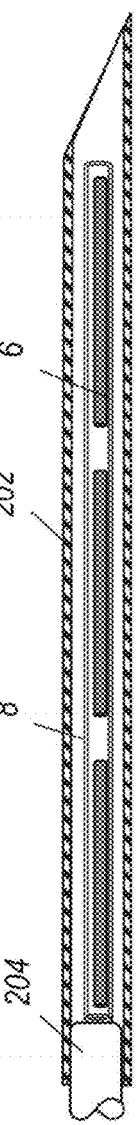
Figure 12:
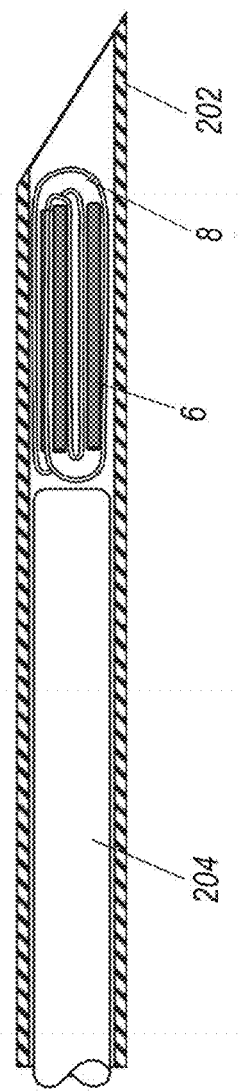
FIG. 12F illustrates a plastically deformable marker for use with the present invention.
Figure 12F:
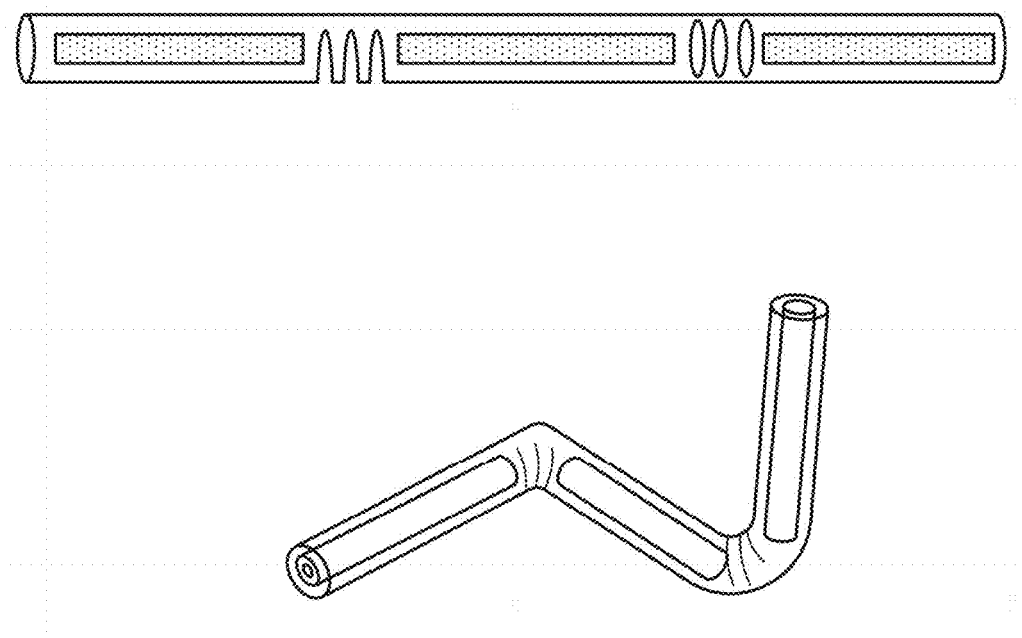

In a further example, the tube or shell containing the magnetic marker material comprises a biocompatible plastically deformable material such as a 316 stainless steel, Titanium, Titanium alloy or similar, such that when it is deployed in the body it plastically deforms from a pre-deployed shape that can fit within a narrow gauge needle e.g. 14 g-18 g to a final deployed shape, as illustrated for example in FIG. 12F.

Further, the shell may function to provide enhanced visibility under ultrasound or X-ray or mammographic imaging. For example, the difference in density of the shell and the space inside the shell provides enhanced echogenicity, and the shell material, if it has a greater mass of material than the marker material inside, will provide increased X-ray visibility. This is particularly beneficial when the magnetic material is a fine wire, for example a glass-coated microwire which has very little mass or size with which to be seen on imaging.

Advantageously, the marker is visible under MRI, but does not form a susceptibility artifact extending beyond the marker more than 10 mm, preferably no more than 5 mm and more preferably no more than 2 mm. Susceptibility artifacts are undesirable as they distort the image in the area surrounding the marker, making it difficult to view the surrounding tissue. For example, an artifact extending 5 mm from the marker may obscure under MRI a sphere of breast tissue of diameter approximately 10 mm. During a course of neo-adjuvant chemotherapy to shrink a tumour prior to surgery, clinicians may wish to monitor the size of the tumour over time using MRI, and also to mark the tumour for later surgical excision. Thus, minimising the extent of the artifact is important so that a minimal volume of tumour is obscured by the artifact.

Thus in a further aspect, the detection system and method may use a marker formed from a magnetic marker material combining a low mass of magnetic alloy, less than 10 milligrams, preferably less than 5 milligrams and more preferably less than 2 milligrams) and a low saturation magnetisation of the alloy. The combination of low mass and low saturation magnetisation means that the marker produces a small artifact on MRI typically of the order of a few mm around the marker.

Figure 11:
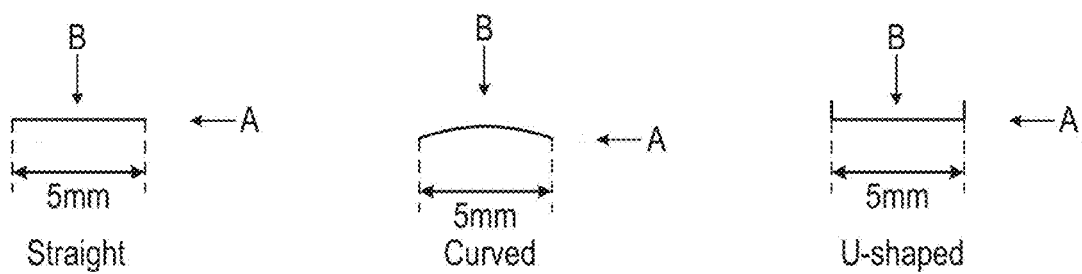
FIG. 11 is a schematic diagram of three shapes of marker for use with the present invention that were investigated to determine that the key dimension is the longest extent of the wire in the direction of sensing.

Table 2 below shows the response of three marker wire shapes (straight, curved and U shaped) shown in FIG. 11 and illustrates that the key dimension is the longest extent of the wire in the direction of sensing. In direction A (see FIG. 11), the Straight and Curved samples have the same sensing distance even though the length of wire in the curved marker is greater, because the maximum magnetic dipole that can be created in each case is the same. Similarly, the U-shaped sample is detectable from the same distance as it has the same dipole length in direction A.

In direction B, the dipole length in the direction is minimal and the sensing distance is greatly reduced for all three samples. However, there is a slight increase in dipole length for the curved and U-shaped samples, resulting in slightly improved detectability.

For the straight wire, the response is broadly shaped like that from a dipole, with a larger response (and larger sensing distance) on or near the axis and a much smaller response transverse to the axis. The magnitude of the response is related to the length of magnetic dipole in the direction of the detection field. On the axis of the wire, the dipole length equals the wire length, and transversely, the dipole length is approximately equal to the diameter of the wire which is much smaller, typically between 10 and 200 microns.

TABLE 2

| Wire sample | Magnetic dipole length in direction A (mm) | Max sensing distance From direction A (mm) | Magnetic dipole length in direction B (mm) | Max sensing distance From direction B (mm) |
|---|---|---|---|---|
| Straight | 5 | 27 | 0.1 | 8 |
| Curved | 5 | 27 | 0.5 | 9.5 |
| U-shaped | 5 | 27 | 1 | 11 |

Further, the harmonic response of the magnetic material can be reduced due to an opposing eddy current generated in the enclosing material. The reduction of the harmonic response in turn affects the markers ability to be detected from greater distances. The opposing eddy current is reduced with increased resistance of the surrounding material e.g. increased material resistivity (see Table 3 below), thinner walled material, partial shells etc.

TABLE 3

| Housing Material | Housing Diameter (mm) | Housing Length (mm) | Housing Material Resistivity ($\Omega$m) | H3 response relative to copper |
|---|---|---|---|---|
| Copper | 0.29 | 4 | $1.7 \times 10^{-8}$ | 1 |
| 316 Stainless Steel | 0.50 | 4 | $7.4 \times 10^{-7}$ | 16 |
| Titanium | 0.51 | 4 | $5.2 \times 10^{-7}$ | 17 |
| Nitinol | 0.33 | 4 | $7.6 \times 10^{-7}$ | 19 |

WO 2016/193753 (Endomagnetics Limited) discloses markers in which the amount of material in the direction of sensing is the significant factor and thus proposes that to obtain a uniform response, the amount of material in any direction should be similar i.e. a sphere would be ideal. This is correct when the property being detected is the bulk susceptibility of the material. However, in the present invention the amount of material in the direction of sensing does not predict the size of the response. For example, the curved marker has more material in direction A than the straight marker, but no greater response. In the present invention, the magnitude of response is determined by the maximum magnetic dipole length that can be provided in the direction of sensing. Thus in one aspect of the present invention the method and system use a deployed marker that provides a similar magnetic dipole length in any direction of sensing so as to provide a uniform magnetic response.

FIGS. 12A to F shows further details of the marker 6 according to the example shown in FIG. 9A together with a deployment system 200. The marker comprises an outer tubular shell 8 and an inner magnetic marker material 6. The outer shell may function to provide a barrier between the magnetic marker material and the body tissue to maintain biocompatibility. Thus the tubular shell is typically formed from a biocompatible material, for example Nitinol, titanium or a polymer. Advantageously to maintain biocompatibility, the ends of the tubular shell are closed.

FIG. 12A shows the magnetic marker formed from a single continuous piece of magnetic marker material 6, and FIG. 12B shows the magnetic marker formed from more than one discrete piece of magnetic marker material 6, for example to facilitate assembly of the marker.

FIG. 12C shows a deployment device 200 comprising a needle 202 and a plunger 204. In use, the needle is inserted into the target tissue under imaging guidance. The deployment device is arranged such that on depression of the plunger, the magnetic marker is deployed from the end of the needle into the target tissue.

FIG. 12D shows a detail of the distal end of the deployment device 200 containing the magnetic marker 6 of FIG. 12B in the needle 202 together with a plunger 204. The magnetic marker is in an elongated straight configuration, but on deployment reconfigures to the shape shown in FIG. 12B, either through the elasticity of the shell 8 or a shape change property of the shell material 8, for example a shape memory such as that achievable with a Nitinol material.

FIG. 12E shows an alternative configuration of the marker of FIG. 12B where prior to deployment the marker is folded in on itself like a flattened 'Z' shape. On deployment it reconfigures to the configuration of FIG. 12B.

FIG. 12F shows a plastically deformable magnetic marker in which that holds more than one discrete piece of magnetic material each of which is within a biocompatible barrier. The outer shell, holding these discrete biocompatible pieces, is capable of being plastically deformed on deployment in order to form its deployed shape.

It will be clear that through using a similar type of shell with a shape transition, that any of the examples in FIGS. 9A to 9I could similarly be configured to fit within a needle and then reconfigure through a shape transition to form the final marker shape as shown in FIGS. 9A to 9I.

Figure 13A:
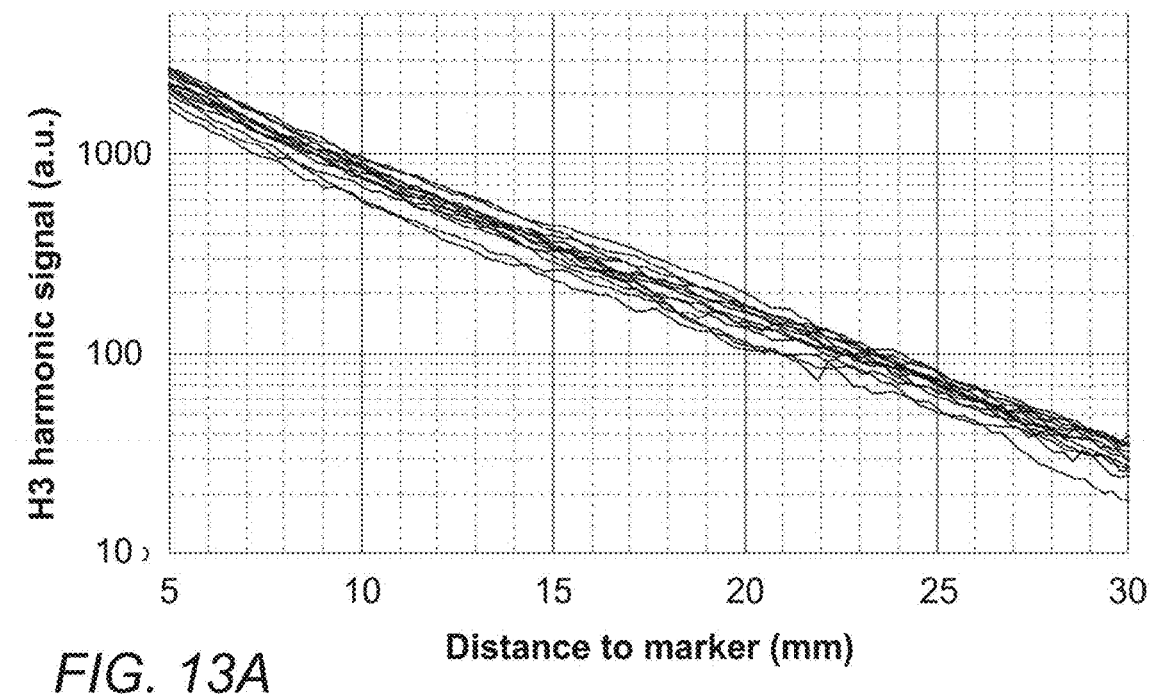
FIG. 13A shows a number of third harmonic response curved from the marker of FIG. 9G at a range of different orientations with respect to a detection probe and FIG. 13B shows the orientations of the marker relative to the detection probe that were tested to produce the graphs of FIG. 13A.
Figure 13B:
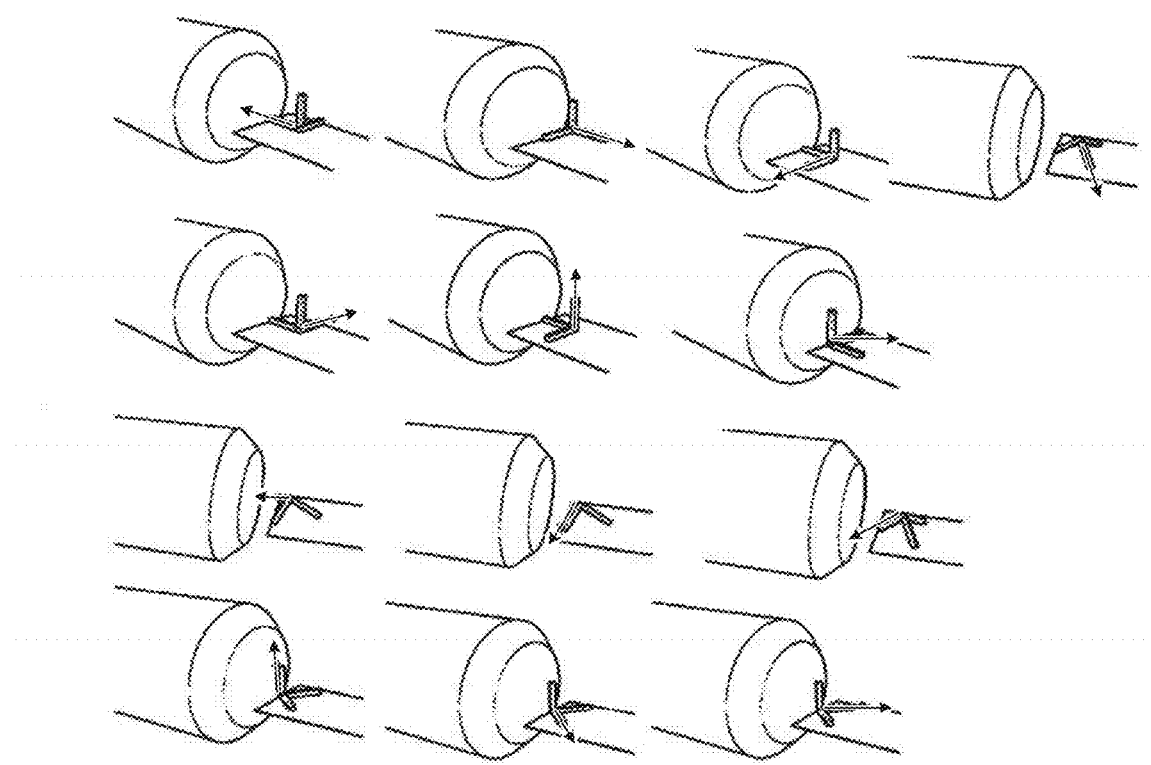

FIG. 13A shows a number of third harmonic response curved from the marker of FIG. 9G (orthogonal tripod) at a range of different orientations with respect to the detection probe. FIG. 13B shows the orientations of the marker relative to the detection probe that were tested to produce the graphs of FIG. 13A. The response at different orientations is substantially similar allowing the distance from the probe to the marker to be calculated regardless of the orientation of the marker. This also provides a less confusing signal to the user as the signal level does not change with orientation or direction.

Figure 14:
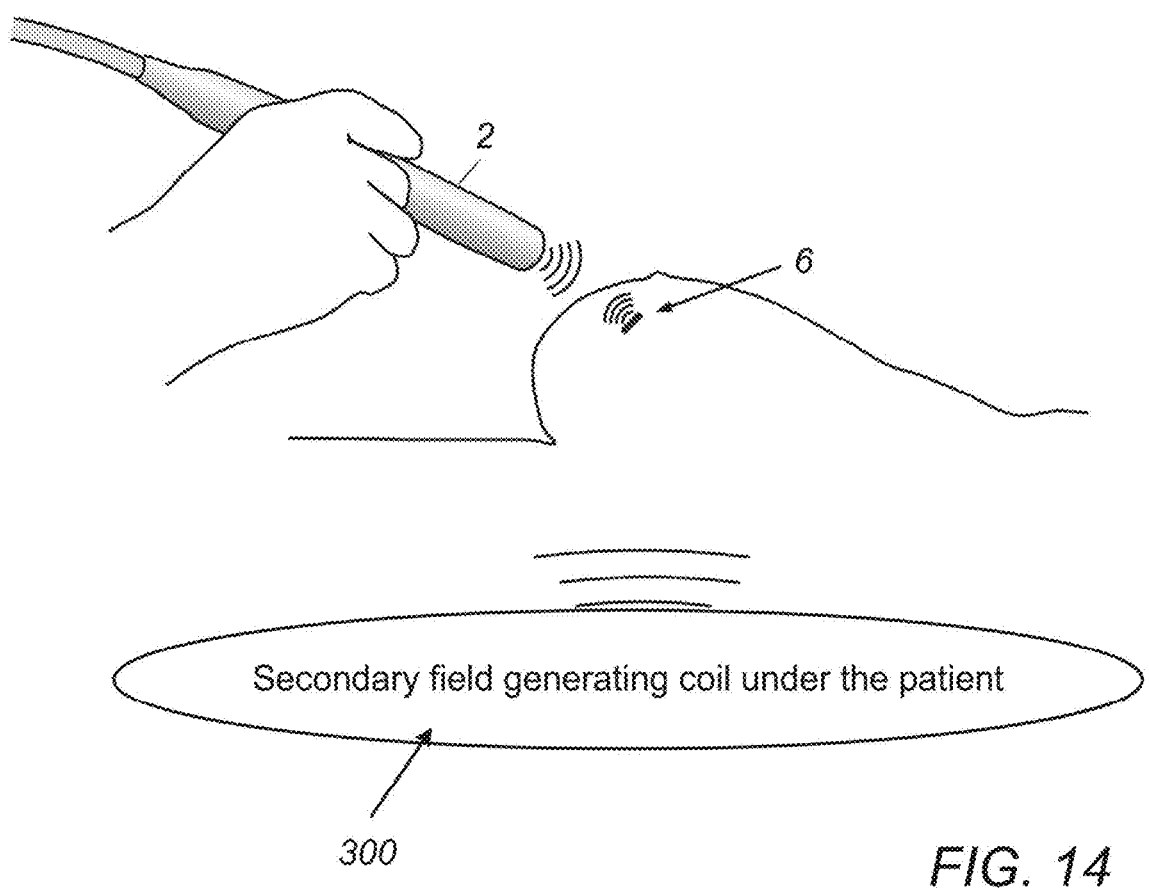
FIG. 14 is a schematic diagram of an alternative embodiment of a detection system according to the present invention.

FIG. 14 shows a further embodiment of a detection system according to the invention where the drive coil is not in a probe, but placed separately elsewhere e.g. in a pad 300 underneath or near the patient during the surgical procedure. The coil may be in the form of a pad containing a coil placed under or near the patient. In this way the size of the coil is not constrained by the size of the handheld probe and can have a larger diameter eg. 100 mm-500 mm to generate a higher magnetic field at the marker site.

The drive coil is connected separately to a drive generator, for example in the detector base unit.

The present invention provides a novel detection system and method for an implantable marker, wherein the marker contains at least a piece of LBJ magnetic material that is excited at a field lower than the bistable switching field and the generated harmonics measured from any direction to determine the position and orientation of the marker. The marker may also be provided below the critical length of the LBJ material required to enable bistable switching behaviour.

The invention claimed is:

1. A detection system for locating a marker in a body, the detection system comprising:
    at least one implantable marker, the implantable marker comprising at least one piece of magnetic material that exhibits a large Barkhausen jump (LBJ) in its magnetisation curve;
    at least one drive coil arranged to excite the marker with an alternating magnetic field and at least one sense coil arranged to detect a signal received from the excited marker;
    a magnetic field generator arranged to drive an alternating magnetic field through the at least one drive coil; and
    at least one detector arranged to receive the signal from the sense coil and detect one or more harmonics of a drive frequency in the received signal, wherein the at least one drive coil excites the marker below the switching field required to initiate bistable switching behaviour of the LBJ material of the marker.

2. The detection system as claimed in claim 1 wherein the implantable marker comprising at least one piece of magnetic material that exhibits a large Barkhausen jump (LBJ) in its magnetisation curve comprises less than 5 mg of LBJ material.

3. The detection system as claimed in claim 1 wherein the implantable marker comprising at least one piece of magnetic material that exhibits a large Barkhausen jump (LBJ) in its magnetization curve is shorter than a critical length required to initiate bistable switching in the LBJ material.

4. The detection system as claimed in claim 3 wherein the marker is <25 mm in length.

5. The detection system as claimed in claim 1 wherein the marker comprises at least one piece of amorphous LBJ material or a LBJ wire configured such that when implanted the magnitude of a harmonic response from the marker when interrogated by an alternating magnetic field is the same, a maximum:minimum ratio≤4, when measured from any direction relative to the marker.

6. The detection system as claimed in claim 5 wherein the marker comprises lengths of the LBJ material along at least orthogonal axes x, y and z.

7. The detection system of claim 1 wherein the LBJ material is coated or provided within a hollow tube.

8. The detection system of claim 1 wherein the marker is deployable from an initial, compact configuration to an extended, deployed configuration.

9. The detection system of claim 1 wherein at least one of the drive and sense coils is provided in a handheld probe.

10. The detection system of claim 1, further comprising an output module configured to process the received harmonic signal and providing at least one indicator to the user relating to a location of the marker relative to the sense coil using a measure of distance from the probe to the marker, the output detection module comprising a harmonic detection circuit.

11. The detection system of claim 1 wherein the system processes one or more aspects of the harmonic response of the marker selected from the magnitude of one or more odd harmonics, even harmonics or a combination of both or the ration of these harmonics to each other or to a fundamental frequency.

12. A method of detecting a marker in a body comprising:
applying an alternating magnetic field to at least one implantable marker comprising at least one piece of magnetic material that exhibits a large Barkhausen jump (LBJ) in its magnetisation curve, wherein the marker is excited below the switching field (HSW) required to initiate bistable switching behaviour of the LBJ material of the marker; and
detecting one or more harmonics of a drive frequency of a signal received from the excited marker caused by a change in magnetization of the marker below its switching field.

13. A method according to claim 12 wherein the drive frequency is above 1 kHz.

14. A method according to claim 12 wherein the drive frequency is in the range 1-100 kHz.

15. A method according to claim 12, further comprising measuring an aspect of the harmonic response of the marker location of the marker.

16. The detection system as claimed in claim 3 wherein the marker is <10 mm in length.

17. The detection system of claim 10 wherein the output module comprises a harmonic detection circuit.

18. The detection system of claim 17 wherein the harmonic detection circuit converts the signal or a modified version thereof to the measure of distance from the probe to the marker such that the marker is localized.

19. A detection system for locating a plurality of different markers in a body; the detection system comprising:
a plurality of implantable markers of different lengths and/or geometries, the implantable markers each comprising at least one piece of magnetic material that exhibits a large Barkhausen jump (LBJ) in its magnetisation curve at a threshold switching field;
at least one drive coil configured to excite the markers with an alternating magnetic field and at least one sense coil configured to detect a signal received from each of the excited markers;
a magnetic field generator configured to drive said alternating magnetic field through the at least one drive coil; and
at least one detector configured to receive the signal from the sense coil and detect a harmonic response comprising one or more harmonics of a drive frequency in the received signal of each of the plurality of markers, wherein the at least one drive coil excites the markers below the threshold switching field required to initiate bistable switching behaviour of the magnetic (LBJ) material of the marker and the detector is configured to detect the received signal of the markers in a sub-bistable mode below the threshold switching field, the harmonic response allowing detection and localisation of the markers below the threshold switching field.

20. The detection system of claim 19, wherein the system is configured to detect a perimeter or margin of a surgical site by detection of the plurality of implantable markers defining the perimeter or margin of the surgical site.

* * * * *